(12) United States Patent
Utsumi et al.

(10) Patent No.: US 8,497,395 B2
(45) Date of Patent: Jul. 30, 2013

(54) COMPOUND

(75) Inventors: Yoshiyuki Utsumi, Kawasaki (JP); Masaru Takeshita, Kawasaki (JP); Yoshitaka Komuro, Kawasaki (JP)

(73) Assignees: Tokyo Ohka Kogyo Co., Ltd., Kawasaki-shi (JP); Central Glass Co., Ltd., Ube-shi (JP)

( * ) Notice: Subject to any disclaimer, the term of this patent is extended or adjusted under 35 U.S.C. 154(b) by 48 days.

(21) Appl. No.: 13/313,993

(22) Filed: Dec. 7, 2011

(65) Prior Publication Data

US 2012/0149916 A1 Jun. 14, 2012

(30) Foreign Application Priority Data

Dec. 8, 2010 (JP) ................ P2010-274069

(51) Int. Cl.
*C07C 211/00* (2006.01)
(52) U.S. Cl.
USPC .............................................. 564/1
(58) Field of Classification Search
USPC ............................................... 564/1
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,444,397 B2 | 9/2002 | Hada et al. | |
| 6,949,325 B2 | 9/2005 | Li et al. | |
| 7,074,543 B2 | 7/2006 | Iwai et al. | |
| 2008/0187860 A1 | 8/2008 | Tsubaki et al. | |
| 2009/0317743 A1 | 12/2009 | Shiono et al. | |
| 2011/0223537 A1 | 9/2011 | Ebata et al. | |

FOREIGN PATENT DOCUMENTS

| | | |
|---|---|---|
| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | A-2003-241385 | 8/2003 |
| JP | A-2005-336452 | 12/2005 |
| JP | A-2006-259582 | 9/2006 |
| JP | A-2006-317803 | 11/2006 |
| JP | A-2008-292975 | 12/2008 |
| JP | A-2010-002870 | 1/2010 |
| WO | WO 2004/074242 A2 | 9/2004 |
| WO | WO 2010/029965 A1 | 3/2010 |

*Primary Examiner* — Johann R Richter
*Assistant Examiner* — Kofi Adzamli
(74) *Attorney, Agent, or Firm* — Knobbe Martens Olson & Bear LLP

(57) ABSTRACT

A compound represented by general formula (c1) ($R^1$ represents an alicyclic group of 5 or more carbon atoms which may have a substituent; X represents a divalent linking group; Y represents a linear, branched or cyclic alkylene group or an arylene group; Rf represents a hydrocarbon group containing a fluorine atom; and $M^+$ represents an organic cation or a metal cation).

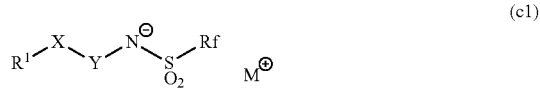

(c1)

1 Claim, No Drawings

COMPOUND

TECHNICAL FIELD

The present invention relates to a novel compound useful as a quencher for a resist composition.

Priority is claimed on Japanese Patent Application No. 2010-274069, filed Dec. 8, 2010, the content of which is incorporated herein by reference.

DESCRIPTION OF RELATED ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified composition is used, which includes a base material component that exhibits a changed solubility in a developing solution under the action of acid and an acid-generator component that generates acid upon exposure.

For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If the resist film formed using the resist composition is selectively exposed during formation of a resist pattern, then within the exposed portions, acid is generated from the acid-generator component, and the action of this acid causes an increase in the solubility of the resin component in an alkali developing solution, making the exposed portions soluble in the alkali developing solution. In this manner, the unexposed portions remain to form a positive resist pattern. The base resin used exhibits increased polarity by the action of acid, thereby exhibiting increased solubility in an alkali developing solution, whereas the solubility in an organic solvent is decreased. Therefore, when such a base resin is applied to a process using a developing solution containing an organic solvent (organic developing solution) (hereafter, this process is referred to as "solvent developing process" or "negative tone-developing process") instead of an alkali developing process, the solubility of the exposed portions in an organic developing solution is decreased. As a result, in the solvent developing process, the unexposed portions of the resist film are dissolved and removed by the organic developing solution, and a negative resist pattern in which the exposed portions are remaining is formed. The negative tone-developing process is proposed, for example, in Patent Document 1.

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm (for example, see Patent Document 2).

On the other hand, as acid generators usable in a chemically amplified resist composition, various types have been proposed including, for example, onium salt acid generators; oxime sulfonate acid generators; diazomethane acid generators; nitrobenzylsulfonate acid generators; iminosulfonate acid generators; and disulfone acid generators. Among these, as the onium salt acid generators, iodonium salts having an iodonium ion as the cation or sulfonium salts having a sulfonium ion as the cation have been conventionally used.

Furthermore, currently, in addition to the base resin and the acid generator, a nitrogen-containing organic compound such as an alkylamine, an alkylalcoholamine or the like is added to chemically amplified resist compositions. The nitrogen-containing organic compound functions as a quencher which traps the acid generated from the acid generator, and contributes to improving various lithography properties.

In recent years, as quenchers, studies have been made on photo-decomposable base which are decomposed by light or radiation. The photo-decomposable base contained in a resist composition functions as a typical quencher at portions unexposed to light or radiation. On the other hand, at portions exposed to light or radiation, the photo-decomposable base itself is decomposed, and hence, the quenching ability is deactivated. As a result, the concentration of acid in exposed portions can be maintained at an appropriate level without undesirable decrease thereof. Patent Document 3 discloses a resist composition including, as the components thereof, a base component containing a polymer having a cyclic carbonate structure-containing repeating unit, an acid generator and an acid diffusion inhibitor having a carbamate structure.

DOCUMENTS OF RELATED ART

Patent Document

[Patent Document 1] Japanese Unexamined Patent Application, First Publication No. 2008-292975
[Patent Document 2] Japanese Unexamined Patent Application, First Publication No. 2003-241385
[Patent Document 3] WO 2010/029965

SUMMARY OF THE INVENTION

As further progress is made in lithography techniques and miniaturization of resist patterns, further improvement in resist materials has been demanded in terms of various lithography properties, resist pattern shape and suppression of pattern collapse. Examples of lithography properties which has been demanded to improve are, for example, line width roughness (LWR), EL margin, and the like.

However, when a conventional photo-decomposable base (light or radiation-decomposable, nitrogen-containing organic compound) as that disclosed in Patent Document 3 was used, there was still room for further improvement in the lithography properties of the obtained resist pattern, the shape of the resist pattern and suppression of pattern collapse.

The present invention takes the above circumstances into consideration, with an object of providing a novel compound useful as a quencher for a resist composition.

For solving the above-mentioned problems, the present invention employs the following aspects.

Specifically, a first aspect of the present invention is a compound represented by general formula (c1) shown below.

[Chemical Formula 1.]

(c1)

$R^1$ represents an alicyclic group of 5 or more carbon atoms which may have a substituent; X represents a divalent linking group; Y represents a linear, branched or cyclic alkylene group or an arylene group; Rf represents a hydrocarbon group containing a fluorine atom; and $M^+$ represents an organic cation or a metal cation.

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with fluorine atom(s).

The term "structural unit" refers to a monomer unit that contributes to the formation of a polymeric compound (resin, polymer, copolymer).

An "acrylate ester" refers to a compound in which the terminal hydrogen atom of the carboxy group of acrylic acid ($CH_2$=CH—COOH) has been substituted with an organic group.

A "structural unit derived from an acrylate ester" refers to a structural unit that is formed by the cleavage of the ethylenic double bond of an acrylate ester.

Examples of the substituent bonded to the carbon atom on the α-position in the "acrylate ester which may have the hydrogen atom bonded to the carbon atom on the α-position substituted with a substituent" include a halogen atom, an alkyl group of 1 to 5 carbon atoms, a halogenated alkyl group of 1 to 5 carbon atoms and a hydroxyalkyl group. With respect to the "structural unit derived from an acrylate ester", the "α-position (the carbon atom on the α-position)" refers to the carbon atom having the carbonyl group bonded thereto, unless specified otherwise.

Examples of the halogen atom as the substituent include a fluorine atom, a chlorine atom, a bromine atom and an iodine atom.

Specific examples of the alkyl group of 1 to 5 carbon atoms as the substituent include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group of 1 to 5 carbon atoms for the substituent include groups in which part or all of the hydrogen atoms of the aforementioned "alkyl group of 1 to 5 carbon atoms for the substituent" are substituted with halogen atoms. Examples of the halogen atom include a fluorine atom, a chlorine atom, a bromine atom and an iodine atom, and a fluorine atom is particularly desirable.

Specific examples of the hydroxyalkyl group of 1 to 5 carbon atoms for the substituent include groups in which part or all of the hydrogen atoms of the aforementioned "alkyl group of 1 to 5 carbon atoms for the substituent" are substituted with hydroxy groups.

In the present invention, it is preferable that a hydrogen atom, an alkyl group of 1 to 5 carbon atoms or a halogenated alkyl group of 1 to 5 carbon atoms is bonded to the carbon atom on the α-position, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

The term "exposure" is used as a general concept that includes irradiation with any form of radiation.

According to the present invention, there is provided a novel compound useful as a quencher for a resist composition.

DETAILED DESCRIPTION OF THE INVENTION

The compound of the present invention is a compound represented by general formula (c1) shown below (hereafter, referred to as "compound (C1)").

[Chemical Formula 2.]

(c1)

$R^1$ represents an alicyclic group of 5 or more carbon atoms which may have a substituent; X represents a divalent linking group; Y represents a linear, branched or cyclic alkylene group or an arylene group; Rf represents a hydrocarbon group containing a fluorine atom; and $M^+$ represents an organic cation or a metal cation.

(Anion Moiety of Compound (C1))

In formula (c1), $R^1$ represents an alicyclic group of 5 or more carbon atoms which may have a substituent. The term "alicyclic group" describes a monocyclic group or polycyclic group that has no aromaticity. The alicyclic group preferably has 5 to 30 carbon atoms, and more preferably 5 to 15 carbon atoms.

The alicyclic group for $R^1$ may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "alicyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated.

As the alicyclic group of 5 or more carbon atoms, for example, a group in which one or more hydrogen atoms have been removed from a monocycloalkane or a polycycloalkane such as a bicycloalkane, a tricycloalkane or a tetracycloalkane can be used. More specific examples include groups in which one or more hydrogen atoms have been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

In the present invention, among these examples, as $R^1$, a group in which one or more hydrogen atoms have been removed from a polycycloalkane is preferable, and a group in which one or more hydrogen atoms have been removed from adamantane is more preferable.

In formula (c1), Y represents a linear, branched or cyclic alkylene group or an arylene group.

The linear or branched alkylene group preferably has 1 to 10 carbon atoms, more preferably 1 to 8, and still more preferably 1 to 5.

Specific examples of the linear alkylene group include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

Specific examples of the branched alkylene group include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The cyclic alkylene group preferably has 3 to 20 carbon atoms, and more preferably 3 to 12 carbon atoms. Examples of the cyclic alkylene group other than those which links by the ring skeleton itself include groups in which the cyclic alkylene group is bonded to the terminal of the aforementioned chain-like alkylene group or groups in which the cyclic alkylene group is interposed within the aforementioned chain-like alkylene group.

The cyclic alkylene group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

Examples of the arylene group for Y include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

In the present invention, among these examples, as Y, a linear or branched alkylene group of 1 to 5 carbon atoms is preferable, and a methylene group, an ethylene group, a trimethylene group or a tetramethylene group is more preferable.

In formula (c1), X represents a divalent linking group.

Preferable examples of the divalent linking group for X include a divalent hydrocarbon group which may have a substituent (more preferably a divalent hydrocarbon group which has a substituent) and a divalent linking group containing a hetero atom.

A hydrocarbon "has a substituent" means that part or all of the hydrogen atoms within the hydrocarbon group is substituted with groups or atoms other than hydrogen.

The hydrocarbon group may be either an aliphatic hydrocarbon group or an aromatic hydrocarbon group. An "aliphatic hydrocarbon group" refers to a hydrocarbon group that has no aromaticity.

The aliphatic hydrocarbon group may be saturated or unsaturated. In general, the aliphatic hydrocarbon group is preferably saturated.

As examples of the hydrocarbon group for X, a linear or branched aliphatic hydrocarbon group, and an aliphatic hydrocarbon group containing a ring in the structure thereof can be given. Specific examples thereof include the linear, branched or cyclic alkylene groups described above for Y, and any combination of the linear, branched or cyclic alkylene groups described above for Y.

The chain-like or cyclic aliphatic hydrocarbon group preferably has a substituent. Examples of the substituent include a fluorine atom, a fluorinated alkyl group of 1 to 5 carbon atoms, and an oxygen atom (=O).

Examples of the aromatic hydrocarbon group as the hydrocarbon group for X include the arylene groups described above for Y. Further, as preferable examples of X, aromatic hydrocarbon groups in which part of the carbon atoms constituting the ring of the aforementioned divalent aromatic hydrocarbon group has been substituted with a hetero atom such as an oxygen atom, a sulfur atom or a nitrogen atom can be given.

The aromatic hydrocarbon group preferably has part or all of the hydrogen atoms constituting the hydrocarbon group substituted with a substituent. Examples of the substituent include an alkyl group of 1 to 5 carbon atoms, a fluorine atom, a fluorinated alkyl group of 1 to 5 carbon atoms, and an oxygen atom (=O).

With respect to a "divalent linking group containing a hetero atom" for X, a hetero atom is an atom other than carbon and hydrogen, and examples thereof include an oxygen atom, a nitrogen atom, a sulfur atom and a halogen atom.

Specific examples of the divalent linking group containing a hetero atom include —O—, —C(=O)—, —C(=O)—O—, a carbonate bond (—O—C(=O)—O—), —NH—, —$NR^{04}$— ($R^{04}$ represents an alkyl group), —NH—C(=O)—, and =N—. Further, a combination of any one of these "divalent linking groups containing a hetero atom" with a divalent hydrocarbon group can also be used. As examples of the divalent hydrocarbon group, the same groups as those described above for the hydrocarbon group which may have a substituent can be given, and a linear or branched aliphatic hydrocarbon group or an aliphatic hydrocarbon group containing a ring in the structure thereof is preferable.

X may or may not have an acid dissociable portion in the structure thereof.

An "acid dissociable portion" refers to a portion within the organic group which is dissociated from the organic group by the action of acid generated upon exposure. When X has an acid dissociable portion, it is preferable that the acid dissociable portion has a tertiary carbon atom.

In the present invention, as X, a divalent linking group containing a hetero atom is preferable.

When X represents a divalent linking group containing a hetero atom, preferable examples of the linking group include —O—, —C(=O)—O—, —C(=O)—NH—, —C(=O)—, —O—C(=O)—O—, and a group represented by general formula -A-O—, —O-A-O—, -[A-C(=O)—O]$_m$— or -A-O—C(=O)— (in the formulas, A represents a divalent hydrocarbon group which may have a substituent, O represents an oxygen atom and m represents an integer of 0 to 3).

In the formulas -A-O—, —O-A-O—, -[A-C(=O)—O]$_m$- and -A-O—C(=O)—, A represents a divalent hydrocarbon group which may have a substituent. Examples of the divalent hydrocarbon group include the same groups as those described above as the "divalent hydrocarbon group which may have a substituent" for X.

As A, a linear aliphatic hydrocarbon group is preferable, more preferably a linear alkylene group, still more preferably a linear alkylene group of 1 to 5 carbon atoms, and a methylene group or an ethylene group is particularly desirable.

In the group represented by the formula -[A-C(=O)—O]$_m$—, m represents an integer of 0 to 3, preferably an integer of 0 to 2, more preferably 0 or 1, and most preferably 1.

As the divalent linking group containing a hetero atom, a linear group containing an oxygen atom and/or nitrogen atom as the hetero atom (e.g., a group containing an ether bond, an ester bond or an amido bond) is preferable, and a group represented by the aforementioned formula —C(=O)—O— or —C(=O)—NH— is more preferable.

In formula (c1), Rf represents a hydrocarbon group containing a fluorine atom.

Examples of the hydrocarbon group containing a fluorine atom for Rf include hydrocarbon groups in which part or all of the hydrogen atoms has been substituted with fluorine atoms. The hydrocarbon group may be either an aliphatic hydrocarbon group or an aromatic hydrocarbon group. The aliphatic hydrocarbon group may be saturated or unsaturated, and may be chain-like or cyclic, but is preferably a linear or branched, saturated aliphatic hydrocarbon group (alkyl group).

The linear alkyl group in which part or all of the hydrogen atoms has been substituted with fluorine atoms preferably has 1 to 10 carbon atoms, more preferably 1 to 5, and still more preferably 1 to 3. Specific examples thereof include a methyl group, an ethyl group, a propyl group, a butyl group, a pentyl group, a hexyl group, a heptyl group, an octyl group, a nonyl group and a decyl group in which part or all of the hydrogen atoms has been substituted with fluorine atoms.

The branched alkyl group in which part or all of the hydrogen atoms has been substituted with fluorine atoms preferably has 3 to 10 carbon atoms, and more preferably 3 to 5. Specific examples thereof include a 1-methylethyl group, a 1-methylpropyl group, a 2-methylpropyl group, a 1-methylbutyl group, a 2-methylbutyl group and a 3-methylbutyl group in which part or all of the hydrogen atoms has been substituted with fluorine atoms.

Among these examples, as Rf, a linear alkyl group in which part or all of the hydrogen atoms has been substituted with fluorine atoms is preferable, a linear perfluoroalkyl group is more preferable, and a trifluoromethyl group, a pentafluoroethyl group or a nonafluoropropyl group is still more preferable.

Specific examples of the compound (C1) are shown below.

[Chemical Formula 3.]

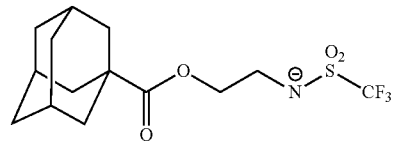
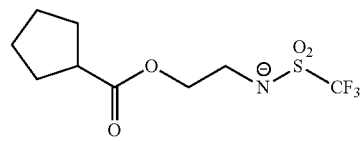
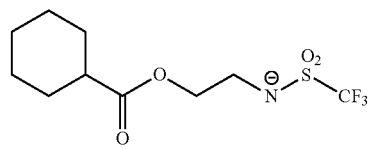
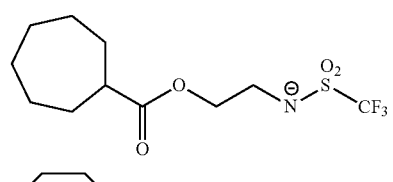
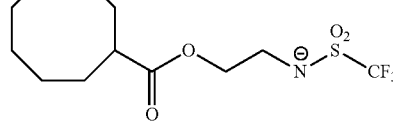
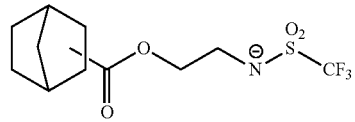
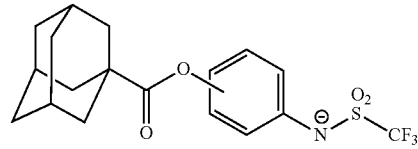
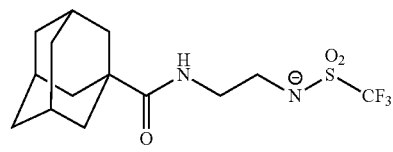
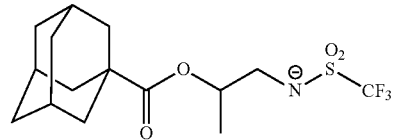
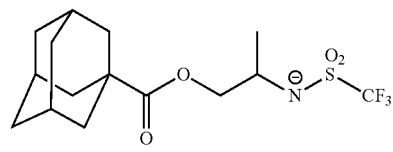

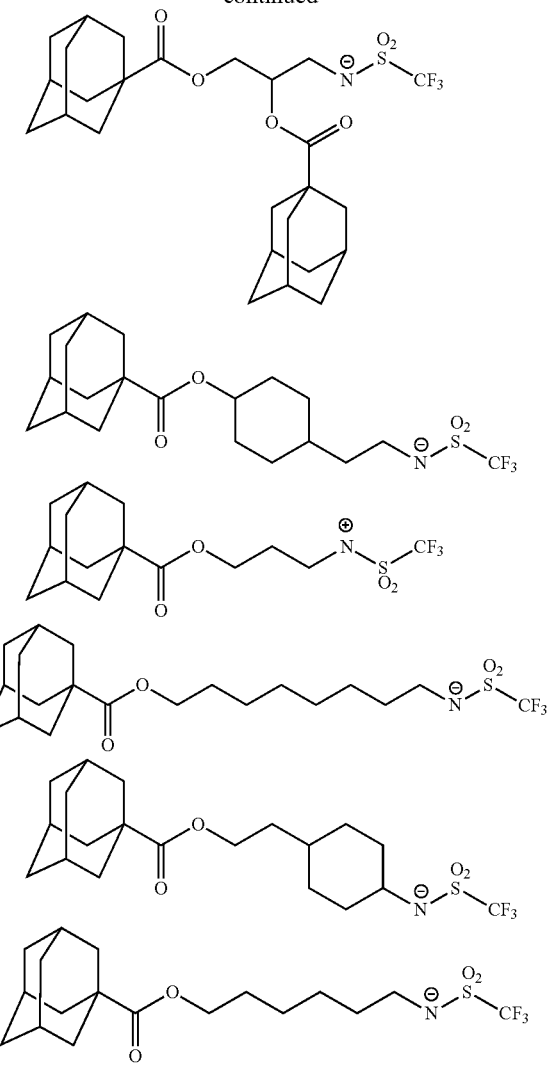

(Cation Moiety of Compound (C1))

In formula (c1), M⁺ represents an organic cation or a metal cation. When M⁺ is an organic cation, the compound (C1) can be used as a photo-decomposable base (light or radiation-decomposable, nitrogen-containing organic compound) which is a quencher for a resist composition. When M⁺ is a metal cation, the compound (C1) can be used as an intermediate compound for producing a photo-decomposable base.

Organic Cation

The organic cation for M⁺ is not particularly limited, and an organic cation conventionally known as the cation moiety of a photo-decomposable base used as a quencher for a resist composition or the cation moiety of an onium salt acid generator for a resist composition can be used.

As the organic cation for M⁺, for example, a cation moiety represented by general formula (c-1) or (c-2) shown below can be used.

[Chemical Formula 4.]

(c-1)

$$R^{2''}-\underset{\underset{R^{3''}}{|}}{\overset{\overset{R^{1''}}{|}}{S^+}}$$

(c-2)

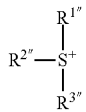

In the formulas, each of $R^{1''}$ to $R^{3''}$, $R^{5''}$ and $R^{6''}$ independently represents an aryl group or an alkyl group, provided that, in formula (c-1), two of $R^{1''}$ to $R^{3''}$ may be mutually bonded to form a ring with the sulfur atom.

In formula (c-1), $R^{1''}$ to $R^{3''}$ each independently represents an aryl group or an alkyl group. In formula (c-1), two of $R^{1''}$ to $R^{3''}$ may be bonded to each other to form a ring with the sulfur atom.

Further, among $R^{1''}$ to $R^{3''}$, it is preferable that at least one group represent an aryl group. Among $R^{1''}$ to $R^{3''}$, it is more preferable that two or more groups are aryl groups, and it is particularly desirable that all of $R^{1''}$ to $R^{3''}$ are aryl groups.

The aryl group for $R^{1''}$ to $R^{3''}$ is not particularly limited. For example, an aryl group having 6 to 20 carbon atoms may be used in which part or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and a naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The halogen atom, with which hydrogen atoms of the aryl group may be substituted, is preferably a fluorine atom.

The alkyl group for $R^{1''}$ to $R^{3''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decyl group, and a methyl group is most preferable because it is excellent in resolution and can be synthesized at a low cost.

When two of $R^{1''}$ to $R^{3''}$ in formula (c-1) are bonded to each other to form a ring with the sulfur atom, it is preferable that the two of $R^{1''}$ to $R^{3''}$ form a 3- to 10-membered ring including the sulfur atom, and it is particularly desirable that the two of $R^{1''}$ to $R^{3''}$ form a 5- to 7-membered ring including the sulfur atom.

When two of $R^{1''}$ to $R^{3''}$ in formula (c-1) are bonded to each other to form a ring with the sulfur atom, the remaining one of $R^{1''}$ to $R^{3''}$ is preferably an aryl group. As examples of the aryl group, the same as the above-mentioned aryl groups for $R^{1''}$ to $R^{3''}$ can be given.

As preferable examples of the cation moiety represented by general formula (c-1), those represented by formulas (I-1-1) to (I-1-11) shown below can be given. Among these, a cation moiety having a triphenylmethane skeleton, such as a cation moiety represented by any one of formulas (I-1-1) to (I-1-9) shown below is particularly desirable.

In formulas (I-1-10) and (I-1-11), each of $R^9$ and $R^{10}$ independently represents a phenyl group or naphthyl group which may have a substituent, an alkyl group of 1 to 5 carbon atoms, an alkoxy group or a hydroxy group.

u is an integer of 1 to 3, and most preferably 1 or 2.

[Chemical Formula 5.]

(I-1-1)
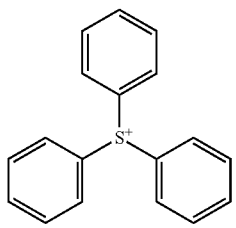

(I-1-2)
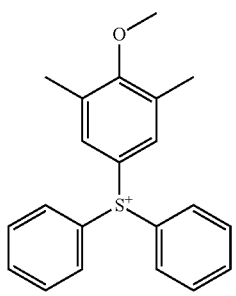

(I-1-3)
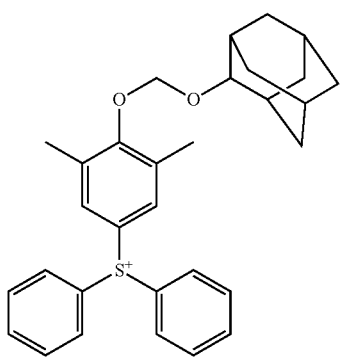

(I-1-4)
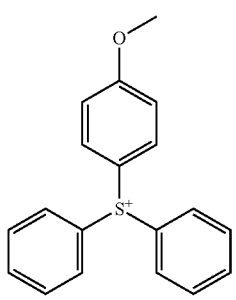

(I-1-5)
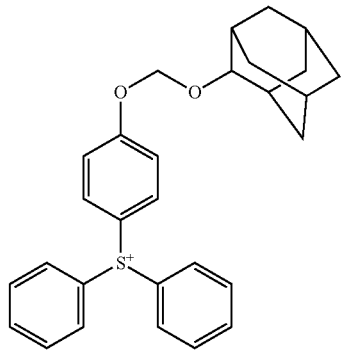

(I-1-6)
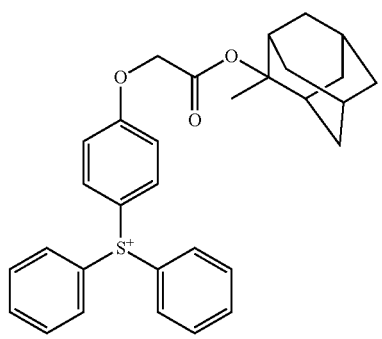

(I-1-7)
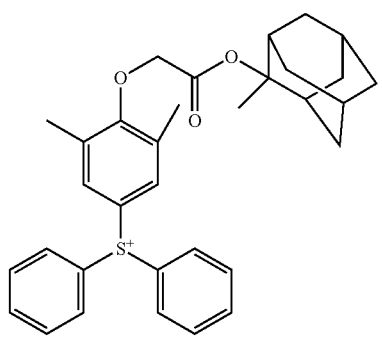

(I-1-8)
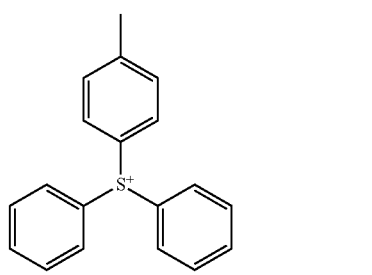

(I-1-9)
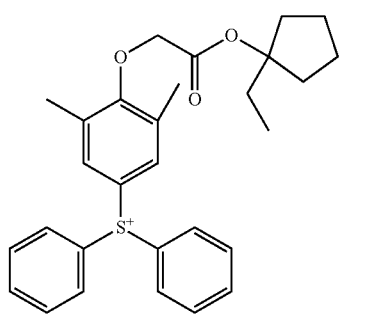

-continued

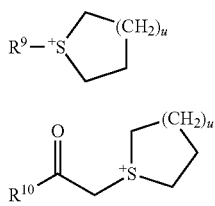

In formula (c-2), $R^{5\prime\prime\prime}$ and $R^{6\prime\prime\prime}$ each independently represent an aryl group or alkyl group. It is preferable that at least one of $R^{5\prime\prime\prime}$ and $R^{6\prime\prime\prime}$ represent an aryl group. It is more preferable that both of $R^{5\prime\prime\prime}$ and $R^{6\prime\prime\prime}$ represent an aryl group.

As the aryl group for $R^{5\prime\prime\prime}$ and $R^{6\prime\prime\prime}$, the same as the aryl groups for $R^{1\prime\prime\prime}$ to $R^{3\prime\prime\prime}$ can be used.

As the alkyl group for $R^{5\prime\prime\prime}$ and $R^{6\prime\prime\prime}$, the same as the alkyl groups for $R^{1\prime\prime\prime}$ to $R^{3\prime\prime\prime}$ can be used.

It is particularly desirable that both of $R^{5\prime\prime\prime}$ and $R^{6\prime\prime\prime}$ represents a phenyl group.

Further, as examples of the organic cation for $M^+$, organic cations represented by general formula (c-3) or (c-4) shown below can also be given.

[Chemical Formula 6.]

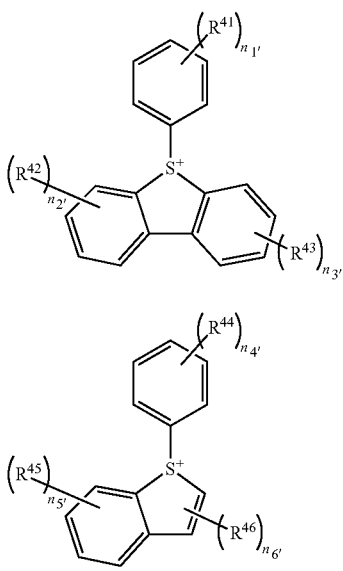

In the formulas, each of $R^{41}$ to $R^{46}$ independently represents an alkyl group, an acetyl group, an alkoxy group, a carboxy group, a hydroxyl group or a hydroxyalkyl group; each of $n_1{}'$ to $n_5{}'$, independently represents an integer of 0 to 3; and $n_6{}'$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert-butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

In formula (c-3) or (c-4), if there are two or more of an individual $R^{41}$ to $R^{46}$ group, as indicated by the corresponding value of $n_1{}'$ to $n_6{}'$, then the two or more of the individual $R^{41}$ to $R^{46}$ group may be the same or different from each other.

$n_1{}'$ is preferably 0 to 2, more preferably 0 or 1, and still more preferably 0.

It is preferable that $n_2{}'$ and $n_3{}'$ each independently represent 0 or 1, and more preferably 0.

$n_4{}'$ is preferably 0 to 2, and more preferably 0 or 1.
$n_5{}'$ is preferably 0 or 1, and more preferably 0.
$n_6{}'$ is preferably 0 or 1, and more preferably 1.

In the present invention, as the organic cation for $M^+$, an organic cation represented by the aforementioned formula (c-1), (c-3) or (c-4) is preferable, and an organic cation represented by the aforementioned formula (c-1) or (c-4) is more preferable.

Metal Cation

The metal ion for $M^+$ is not particularly limited, and is preferably an alkali metal ion. Specific examples of alkali metal ions include a sodium ion, a lithium ion and a potassium ion, and a sodium ion or a lithium ion is more preferable.

(Production Method of Compound (C1))

The production method of the compound (C1) of the present invention is not particularly limited. For example, in the case where X in formula (c1) is a group having an oxygen atom on the terminal thereof which is bonded to Y, the compound (C1) represented by general formula (c1) can be produced by reacting a compound (i-1) represented by general formula (i-1) shown below with a compound (i-2) represented by general formula (i-2) shown below to obtain a compound (i-3) represented by general formula (i-3), and reacting the compound (i-3) with a compound $Z^-M^+$ (a compound represented by general formula (i-4) shown below) having the desired cation $M^+$, thereby obtaining the compound (C1).

[Chemical Formula 7.]

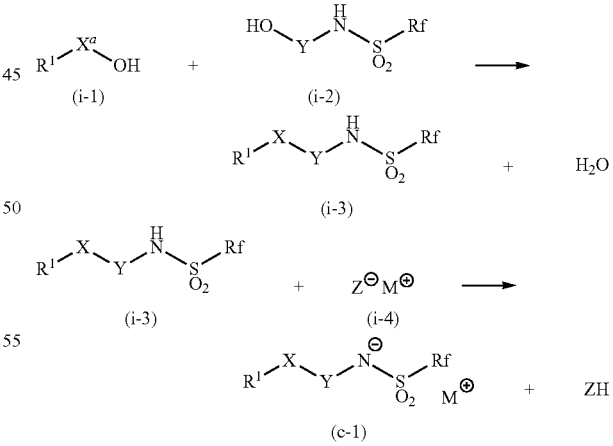

In the formulas, $R^1$, X, Y, Rf and $M^+$ are respectively the same as defined for $R^1$, X, Y, Rf and $M^+$ in the aforementioned general formula (c1). $X^a$ represents a group in which the terminal oxygen atom has been removed from the X group, and $Z^-$ represents a counteranion.

Firstly, the compound (i-1) is reacted with the compound (i-2), to thereby obtain the compound (i-3).

In formula (i-1), $R^1$ is the same as defined above, and $X^a$ represents a group in which the terminal oxygen atom has been removed from the X group. In formula (i-2), Y and Rf are the same as defined above.

As the compound (i-1) and the compound (i-2), commercially available compounds may be used, or the compounds may be synthesized.

The method for reacting the compound (i-1) with the compound (i-2) to obtain the compound (i-3) is not particularly limited, but can be performed, for example, by reacting the compound (i-1) with the compound (i-2) in an organic solvent in the presence of an appropriate acidic catalyst, followed by washing and recovering the reaction mixture.

The acidic catalyst used in the above reaction is not particularly limited, and examples thereof include toluenesulfonic acid and the like. The amount of the acidic catalyst is preferably 0.05 to 5 moles, per 1 mole of the compound (i-2).

As the organic solvent used in the above reaction, any organic solvent which is capable of dissolving the raw materials, i.e., the compound (i-1) and the compound (i-2) can be used, and specific examples thereof include toluene and the like. The amount of the organic solvent is preferably 0.5 to 100 parts by weight, more preferably 0.5 to 20 parts by weight, relative to the amount of the compound (i-1). As the organic solvent, one type may be used alone, or two or more types may be used in combination.

In general, the amount of the compound (i-2) used in the above reaction is preferably 0.5 to 5 moles per 1 mole of the compound (i-1), and more preferably 0.8 to 4 moles per 1 mole of the compound (i-1).

The reaction time depends on the reactivity of the compounds (i-1) and (i-2), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

Next, the obtained compound (i-3) is reacted with the compound (i-4), thereby obtaining the compound (C1).

In formula (i-4), $M^+$ is the same as defined above, and $Z^-$ represents a counteranion.

The method for reacting the compound (i-3) with the compound (i-4) to obtain the compound (C1) is not particularly limited, but can be performed, for example, by dissolving the compound (i-3) in an organic solvent and water in the presence of an appropriate alkali metal hydroxide, followed by addition of the compound (i-4) and stirring.

The alkali metal hydroxide used in the above reaction is not particularly limited, and examples thereof include sodium hydroxide, potassium hydroxide and the like. The amount of the alkali metal hydroxide is preferably 0.3 to 3 moles, per 1 mole of the compound (i-3).

Examples of the organic solvent used in the above reaction include dichloromethane, chloroform, ethyl acetate and the like. The amount of the organic solvent is preferably 0.5 to 100 parts by weight, and more preferably 0.5 to 20 parts by weight, relative to the weight of the compound (i-3). As the solvent, one type may be used alone, or two or more types may be used in combination.

In general, the amount of the compound (i-4) used in the above reaction is preferably 0.5 to 5 moles per 1 mole of the compound (i-3), and more preferably 0.8 to 4 moles per 1 mole of the compound (i-3).

The reaction time depends on the reactivity of the compounds (i-3) and (i-4), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

After the reaction, the compound (C1) contained in the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound of the present invention obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

As described above, the compound (C1) of the present invention is useful as a photo-decomposable base for a resist composition or an intermediate of the photo-decomposable base. As an example of a resist composition containing a compound (C1) having an organic cation as the cation moiety (hereafter, such a compound (C1) is referred to as "component (C11)"), the below-described resist composition can be given. When the compound (C1) has a metal cation as the cation moiety (hereafter, such a compound (C1) is referred to as "component (C12)"), the metal cation of the component (C12) can be exchanged to a desired organic cation to obtain a component (C11), and the component (C11) can be used for a resist composition. The method for exchanging the metal cation to an organic cation is not particularly limited, and can be performed, for example, by adding a compound "$M'^+A^-$ consisting of a desired organic cation $M'^+$ and a counteranion $A^-$ and the component (C12) to an appropriate organic solvent and pure water, followed by stirring, washing the reaction mixture and recovering.

<<Resist Composition>>

In addition to the aforementioned component (C11), the resist composition preferably contains a base component (A) which exhibits changed solubility in an alkali developing solution under action of acid (hereafter, referred to as "component (A)") and an acid-generator component (B) which generates acid upon exposure (hereafter, referred to as "component (B)").

With respect to a resist film formed using the resist composition, when a selective exposure is conducted during formation of a resist pattern, acid is generated from the component (B) and the component (C11), and the generated acid acts on the component (A) to change the solubility of the component (A) in a developing solution. As a result, the solubility of the exposed portions in a developing solution is changed, whereas the solubility of the unexposed portions in a developing solution remains unchanged. Therefore, the exposed portions are dissolved and removed by alkali developing in the case of a positive pattern, whereas unexposed portions are dissolved and removed in the case of a negative pattern, and hence, a resist pattern can be formed.

The resist composition may be either a negative resist composition or a positive resist composition.

In the present specification, a resist composition which forms a positive pattern by dissolving and removing the exposed portions is called a positive resist composition, and a resist composition which forms a negative pattern by dissolving and removing the unexposed portions is called a negative resist composition.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The "organic compound having a molecular weight of 500 or more" which can be used as a base component is broadly classified into non-polymers and polymers.

In general, as a non-polymer, any of those which have a molecular weight in the range of 500 to less than 4,000 is used. Hereafter, a non-polymer having a molecular weight in the range of 500 to less than 4,000 is referred to as a low molecular weight compound.

As a polymer, any of those which have a molecular weight of 1,000 or more is generally used. Hereafter, a polymer having a molecular weight of 1,000 or more is referred to as a polymeric compound. With respect to a polymeric compound, the "molecular weight" is the weight average molecular weight in terms of the polystyrene equivalent value determined by gel permeation chromatography (GPC). Hereafter, a polymeric compound is frequently referred to simply as a "resin".

As the component (A), a resin component which exhibits changed solubility in a developing solution under action of acid may be used. Alternatively, as the component (A), a low molecular weight material which exhibits changed solubility in a developing solution under action of acid may be used.

When the resist composition of the present invention is a "negative resist composition for alkali developing process" which forms a negative pattern in an alkali developing process, for example, as the component (A), a base component that is soluble in an alkali developing solution is used, and a cross-linking agent is blended in the negative resist composition.

In the negative resist composition for alkali developing process, when acid is generated from the component (B) and (C11) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition for alkali developing process, a resin that is soluble in an alkali developing solution (hereafter, referred to as "alkali-soluble resin") is used.

Examples of the alkali soluble resin include a resin having a structural unit derived from at least one of α-(hydroxyalkyl) acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; an acrylic resin which has a sulfonamide group and may have the hydrogen atom bonded to the carbon atom on the α-position substituted with a substituent or polycycloolefin resin having a sulfoneamide group, as disclosed in U.S. Pat. No. 6,949,325; an acrylic resin which may have the hydrogen atom bonded to the carbon atom on the α-position substituted with a substituent and having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linker added is preferably within a range from 1 to 50 parts by weight, relative to 100 parts by weight of the alkali-soluble resin.

In the case of a resist composition which forms a positive pattern in an alkali developing process and a negative pattern in the case of a solvent developing process, it is preferable to use a base component (A0) (hereafter, referred to as "component (A0)") which exhibits increased polarity by the action of acid. By using the component (A0), since the polarity of the base component changes prior to and after exposure, an excellent development contrast can be obtained not only in an alkali developing process, but also in a solvent developing process.

More specifically, in the case of applying an alkali developing process, the component (A0) is substantially insoluble in an alkali developing solution prior to exposure, but when acid is generated from the component (B) and the component (C11) upon exposure, the action of this acid causes an increase in the polarity of the base component, thereby increasing the solubility of the component (A0) in an alkali developing solution. Therefore, in the formation of a resist pattern, by conducting selective exposure of a resist film formed by applying the resist composition to a substrate, the exposed portions changes from an insoluble state to a soluble state in an alkali developing solution, whereas the unexposed portions remain insoluble in an alkali developing solution, and hence, a positive resist pattern can be formed by alkali developing.

On the other hand, in the case of a solvent developing process, the component (A0) exhibits high solubility in an organic developing solution prior to exposure, and when acid is generated from the component (B) and the component (C11) upon exposure, the polarity of the component (A0) is increased by the action of the generated acid, thereby decreasing the solubility of the component (A0) in an organic developing solution. Therefore, in the formation of a resist pattern, by conducting selective exposure of a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be made between the exposed portions and unexposed portions, thereby enabling the formation of a negative resist pattern.

In the resist composition, the component (A) is preferably a base component which exhibits increased polarity by the action of acid (i.e., a component (A0)). That is, the resist composition is preferably a chemically amplified resist composition which becomes a positive type in the case of an alkali developing process, and a negative type in the case of a solvent developing process.

The component (A0) may be a resin component (A1) that exhibits increased polarity under the action of acid (hereafter, frequently referred to as "component (A1)"), a low molecular weight material (A2) that exhibits increased polarity under the action of acid (hereafter, frequently referred to as "component (A2)"), or a mixture thereof.

[Component (A1)]

As the component (A1), a resin component (base resin) typically used as a base component for a chemically amplified resist composition can be used alone, or two or more of such resin components can be mixed together.

The component (A1) preferably has a structural unit derived from an acrylate ester which may have the hydrogen atom bonded to the carbon atom on the α-position substituted with a substituent.

In the resist composition, it is particularly desirable that the component (A1) has a structural unit (a1) derived from an acrylate ester which may have the hydrogen atom bonded to the carbon atom on the α-position substituted with a substituent and contains an acid decomposable group which exhibits increased polarity by the action of acid.

Further, it is preferable that the component (A1) include a structural unit (a2) derived from an acrylate ester containing a lactone-containing cyclic group, and which may have the hydrogen atom bonded to the carbon atom on the α-position substituted with a substituent, as well as the structural unit (a1).

Furthermore, it is preferable that the component (A1) include a structural unit (a3) derived from an acrylate ester containing a polar group-containing aliphatic hydrocarbon group and may have the hydrogen atom bonded to the carbon atom on the α-position substituted with a substituent, as well as the structural unit (a1), or the structural unit (a1) and the structural unit (a2).

(Structural Unit (a1))

The structural unit (a1) is a structural unit derived from an acrylate ester which may have the hydrogen atom bonded to the carbon atom on the α-position substituted with a substituent and contains an acid decomposable group which exhibits increased polarity by the action of acid.

The term "acid decomposable group" refers to a group in which at least a part of the bond within the structure thereof is cleaved by the action of an acid (acid generated from the component (B) upon exposure).

Examples of acid decomposable groups which exhibit increased polarity by the action of an acid include groups which are decomposed by the action of an acid to form a polar group.

Examples of the polar group include a carboxy group, a hydroxy group, an amino group and a sulfo group ($-SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

An "acid dissociable group" is a group in which at least the bond between the acid dissociable group and the adjacent carbon atom is cleaved by the action of an acid (acid generated from the component (B) upon exposure). It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, in the case of applying an alkali developing process, the solubility in an alkali developing solution is relatively increased. On the other hand, in the case of applying a solvent developing process, the solubility in an organic developing solution containing an organic solvent decreases.

As the acid dissociable group for the structural unit (a1), any of those which have been proposed as acid dissociable groups for a base resin of a chemically amplified resist may be used. Generally, groups that form either a cyclic or chain-like tertiary alkyl ester with the carboxyl group of the (meth) acrylic acid, and acetal-type acid dissociable groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(=O)—O—). In this tertiary alkyl ester, the action of acid causes cleavage of the bond between the oxygen atom and the tertiary carbon atom, thereby forming a carboxy group. As a result, the polarity of the component (A1) is increased.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable groups".

Examples of tertiary alkyl ester-type acid dissociable groups include aliphatic branched, acid dissociable groups and aliphatic cyclic group-containing acid dissociable groups.

In the present description and claims, the term "aliphatic branched" refers to a branched structure having no aromaticity.

The "aliphatic branched, acid dissociable group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable group, for example, a group which has a tertiary carbon atom on the ring structure of the cycloalkyl group can be used. Specific examples include groups represented by any one of general formulas (1-1) to (1-9) shown below, such as a 2-methyl-2-adamantyl group and a 2-ethyl-2-adamantyl group.

Further, as examples of aliphatic branched acid dissociable group, groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto, as those represented by general formulas (2-1) to (2-6) shown below, can be given.

[Chemical Formula 8.]

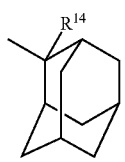
(1-1)

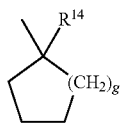
(1-2)

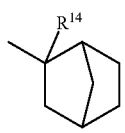
(1-3)

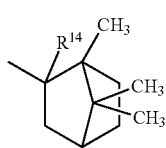
(1-4)

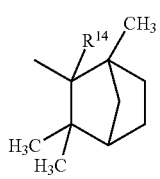
(1-5)

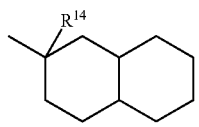
(1-6)

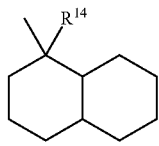
(1-7)

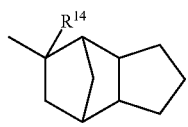
(1-8)

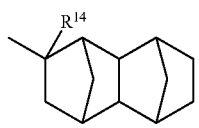
(1-9)

In the formulas above, $R^{14}$ represents an alkyl group; and g represents an integer of 0 to 8.

[Chemical Formula 9.]

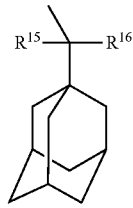
(2-1)

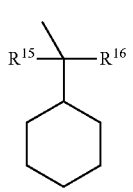
(2-2)

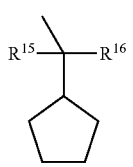
(2-3)

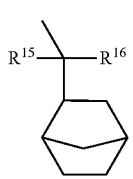
(2-4)

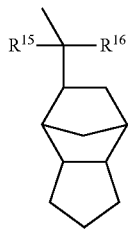

(2-5)

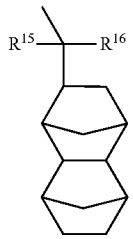

(2-6)

In the formulas, each of $R^{14}$ and $R^{16}$ independently represents an alkyl group (which may be linear or branched, and preferably has 1 to 5 carbon atoms).

As the alkyl group for $R^{14}$, a linear or branched alkyl group is preferable.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group is particularly desirable.

g is preferably an integer of 0 to 3, more preferably 1 to 3, and still more preferably 1 or 2.

As the alkyl group for $R^{15}$ and $R^{16}$, the same alkyl groups as those for $R^{14}$ can be used.

In formulas (1-1) to (1-9) and (2-1) to (2-6), part of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of the substituent include an alkyl group of 1 to 5 carbon atoms, a fluorine atom and a fluorinated alkyl group.

An "acetal-type acid dissociable group" generally substitutes a hydrogen atom at the terminal of an OH-containing polar group such as a carboxy group or hydroxyl group, so as to be bonded with an oxygen atom. When acid is generated upon exposure, the generated acid acts to break the bond between the acetal-type acid dissociable group and the oxygen atom to which the acetal-type, acid dissociable group is bonded, thereby forming an OH-containing polar group such as a carboxy group or a hydroxy group. As a result, the polarity of the component (A1) is increased.

Examples of acetal-type acid dissociable groups include groups represented by general formula (p1) shown below.

[Chemical Formula 10.]

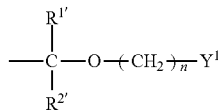

(p1)

In the formula, each of $R^{1'}$ and $R^{2'}$ independently represent a hydrogen atom or an alkyl group of 1 to 5 carbon atoms; n represents an integer of 0 to 3; and $Y^1$ represents an alkyl group of 1 to 5 carbon atoms or an aliphatic cyclic group.

In general formula (p1) above, n is preferably an integer of 0 to 2, more preferably 0 or 1, and most preferably 0.

As the alkyl group of 1 to 5 carbon atoms for $R^{1'}$ and $R^{2'}$, the same alkyl groups of 1 to 5 carbon atoms as those described above for R can be used, although a methyl group or ethyl group is preferable, and a methyl group is particularly desirable.

In particular, it is preferable that at least one of $R^{1'}$ and $R^{2'}$ be a hydrogen atom. That is, it is preferable that the acid dissociable group (p1) is a group represented by general formula (p1-1) shown below.

[Chemical Formula 11.]

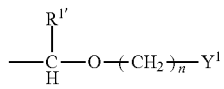

(p1-1)

In the formula, $R^{1'}$, n and $Y^1$ are the same as defined above.

As the alkyl group of 1 to 5 carbon atoms for $Y^1$, the same alkyl groups of 1 to 5 carbon atoms as those described above can be used.

As the aliphatic cyclic group for $Y^1$, any of the aliphatic monocyclic/polycyclic groups which have been proposed for conventional ArF resists and the like can be appropriately selected for use. For example, the same groups described above in connection with the "aliphatic cyclic group" can be used.

Further, as the acetal-type, acid dissociable group, groups represented by general formula (p2) shown below can also be used.

[Chemical Formula 12.]

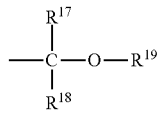

(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable. It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 13.]

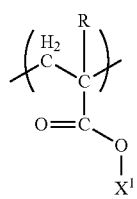

(a1-0-1)

In the formula, R represents a hydrogen atom, an alkyl group of 1 to 5 carbon atoms or a halogenated alkyl group of 1 to 5 carbon atoms; and $X^1$ represents an acid dissociable group.

[Chemical Formula 14.]

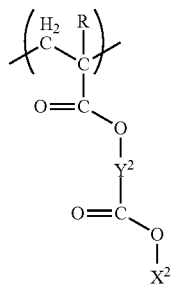

(a1-0-2)

In the formula, R represents a hydrogen atom, an alkyl group of 1 to 5 carbon atoms or a halogenated alkyl group of 1 to 5 carbon atoms; $X^2$ represents an acid dissociable group; and $Y^2$ represents a divalent linking group.

In general formula (a1-0-1) above, the alkyl group of 1 to 5 carbon atoms or halogenated alkyl group of 1 to 5 carbon atoms for R are the same as the alkyl group of 1 to 5 carbon atoms or halogenated alkyl group of 1 to 5 carbon atoms which can be used as the substituent for the hydrogen atom bonded to the carbon atom on the α-position of the aforementioned acrylate ester.

$X^1$ is not particularly limited as long as it is an acid dissociable group. Examples thereof include the aforementioned tertiary alkyl ester-type acid dissociable groups and acetal-type acid dissociable groups, and tertiary alkyl ester-type acid dissociable groups are preferable.

In general formula (a1-0-2), R is the same as defined above.

$X^2$ is the same as defined for $X^1$ in general formula (a1-0-1).

As the divalent linking group for $Y^2$, the same divalent linking groups as those described above for X in the aforementioned formula (c1) can be mentioned. Among these, as $Y^2$, a divalent linking group containing a hetero atom is preferable, and a group represented by formula -A-O—B—, -[A-C(=O)—O]$_m$—B— or -A-O—C(=O)—B— is more preferable.

In the formulas above, A and m are the same as defined above. As B, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 15.]

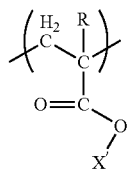

(a1-1)

(a1-2)
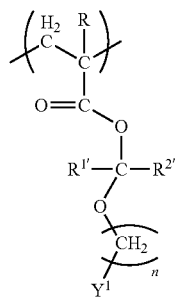

(a1-3)
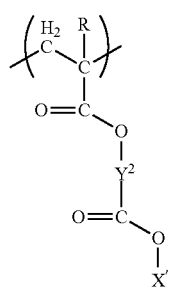

(a1-4)
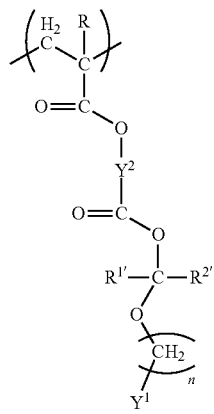

[Chemical Formula 16.]

(a1-1-1)
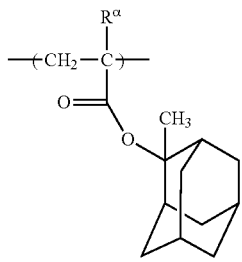

(a1-1-2)
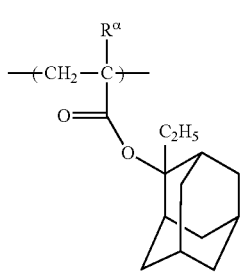

(a1-1-3)
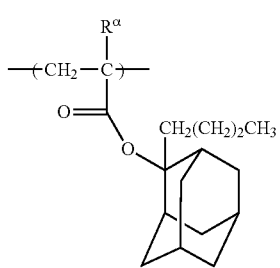

(a1-1-4)
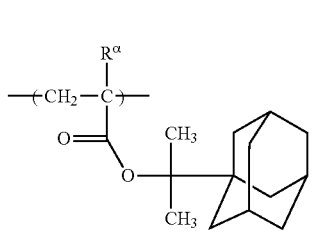

(a1-1-5)
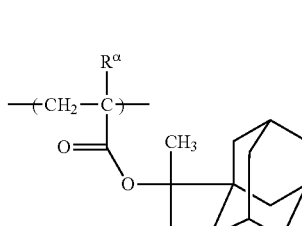

(a1-1-6)
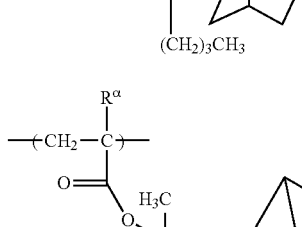

In the formulas, X' represents a tertiary alkyl ester-type acid dissociable group; $Y^1$ represents an alkyl group of 1 to 5 carbon atoms or an aliphatic cyclic group; n represents an integer of 0 to 3; $Y^2$ represents a divalent linking group; R is the same as defined above; and each of $R^{1\prime}$ and $R^{2\prime}$ independently represents a hydrogen atom or an alkyl group of 1 to 5 carbon atoms.

Examples of the tertiary alkyl ester-type acid dissociable group for X' include the same tertiary alkyl ester-type acid dissociable groups as those described above for $X^1$.

$R^{2\prime}$, n and $Y^1$ are respectively the same as defined for $R^{1\prime}$, $R^{2\prime}$, n and $Y^1$ in general formula (p1) described above in connection with the "acetal-type acid dissociable group".

As examples of $Y^2$, the same groups as those described above for $Y^2$ in general formula (a1-0-2) can be given.

Specific examples of structural units represented by general formula (a1-1) to (a1-4) are shown below.

In the formulas shown below, $R^\alpha$ represents a hydrogen atom, a methyl group or a trifluoromethyl group.

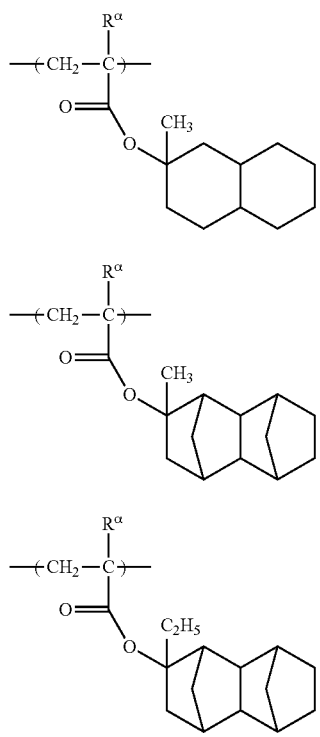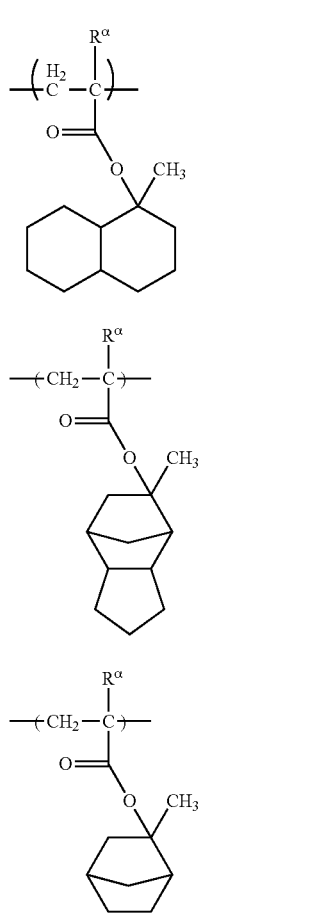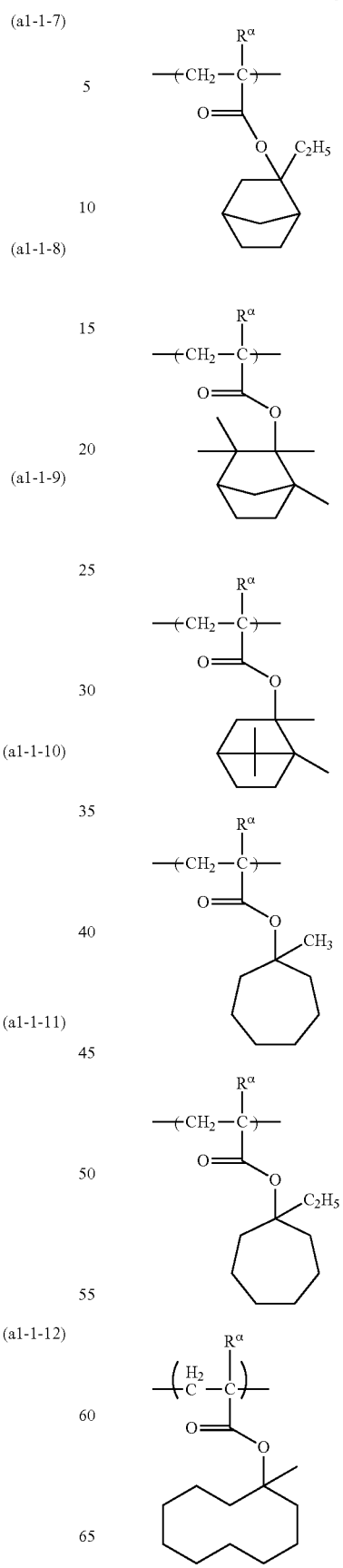

(a1-1-19) 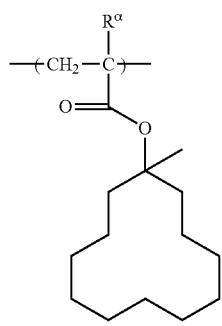
(a1-1-20) 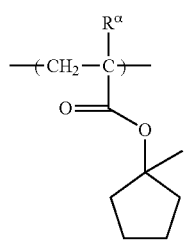
(a1-1-21) 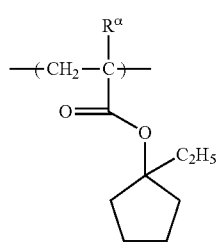
[Chemical Formula 18.]
(a1-1-22) 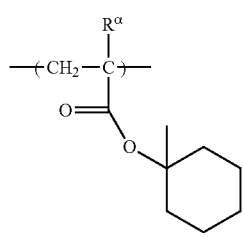
(a1-1-23) 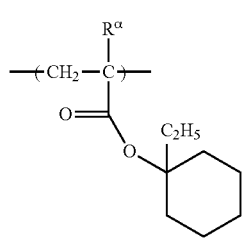
(a1-1-24) 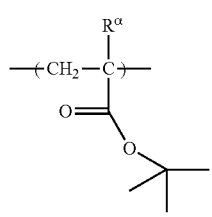
(a1-1-25) 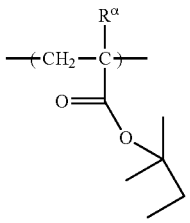
(a1-1-26) 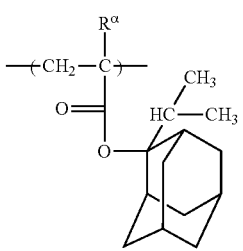
(a1-1-27) 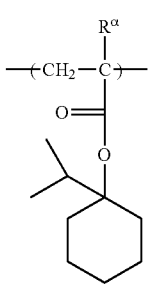
(a1-1-28) 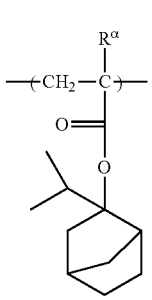
(a1-1-29) 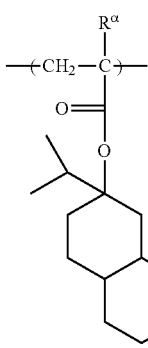

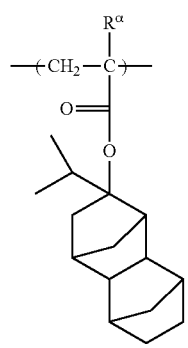 (a1-1-30)
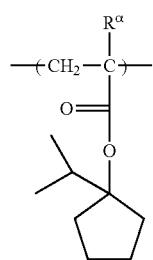 (a1-1-31)
[Chemical Formula 19.]
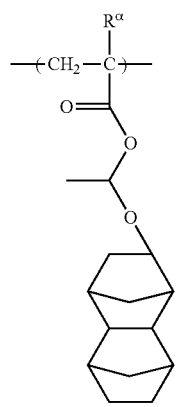 (a1-2-1)
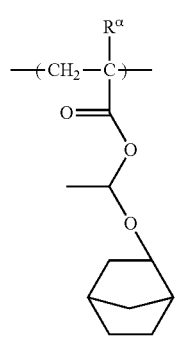 (a1-2-2)
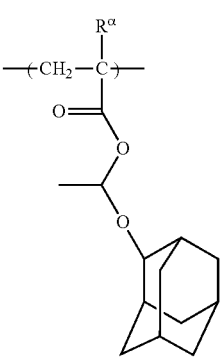 (a1-2-3)
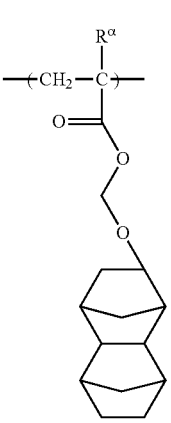 (a1-2-4)
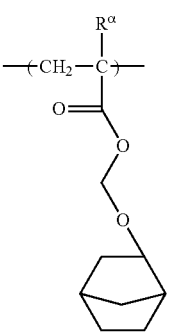 (a1-2-5)
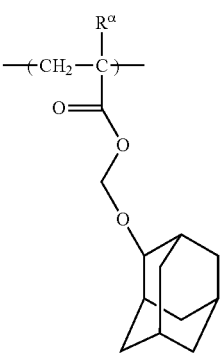 (a1-2-6)

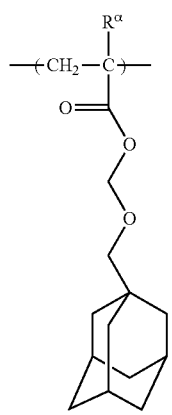
(a1-2-7)
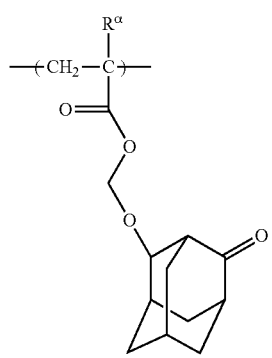
(a1-2-8)
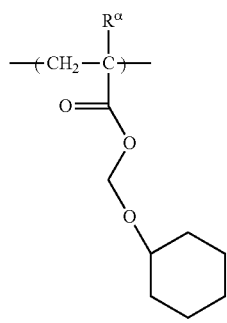
(a1-2-9)
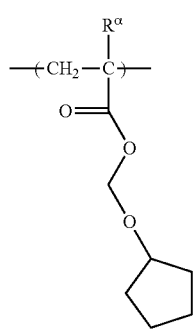
(a1-2-10)
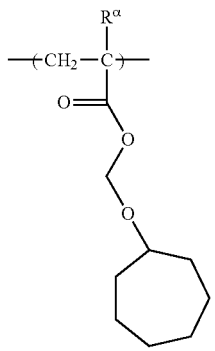
(a1-2-11)
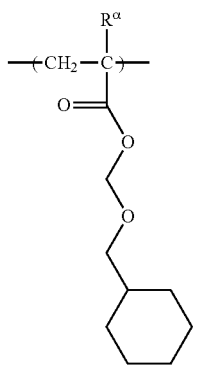
(a1-2-12)
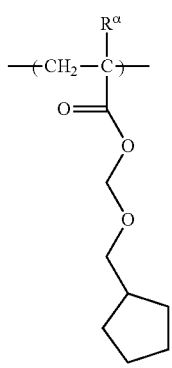
(a1-2-13)
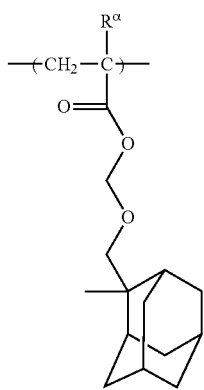
(a1-2-14)

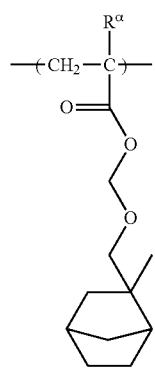 (a1-2-15)
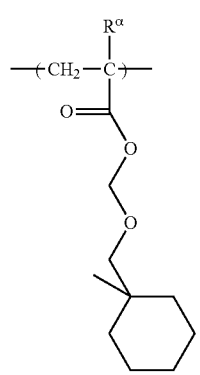 (a1-2-16)
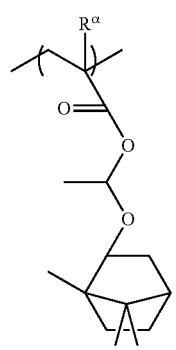 (a1-2-17)
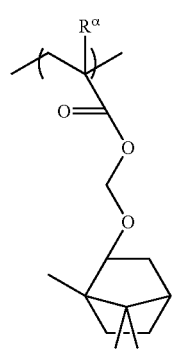 (a1-2-18)
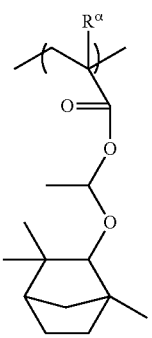 (a1-2-19)
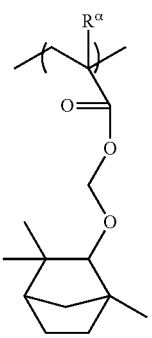 (a1-2-20)
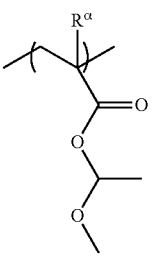 (a1-2-21)
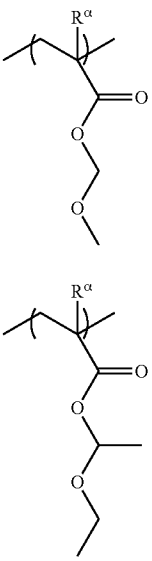 (a1-2-22)
(a1-2-23)

(a1-2-24)
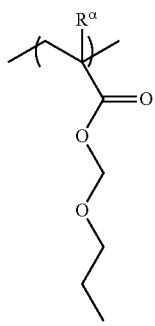
[Chemical Formula 20.]
(a1-3-1)
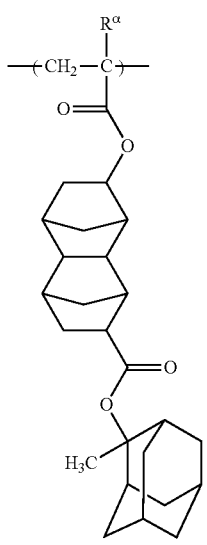
(a1-3-2)
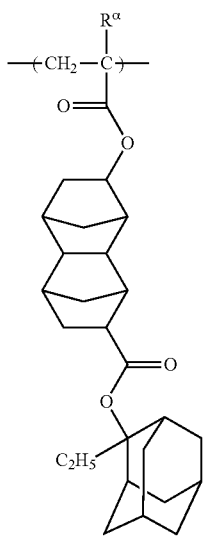
(a1-3-3)
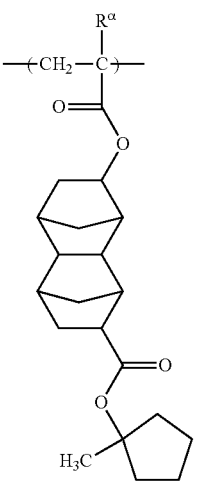
(a1-3-4)
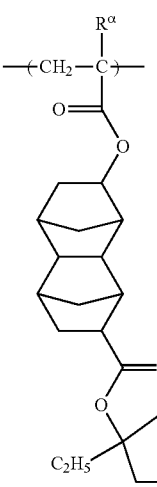
(a1-3-5)
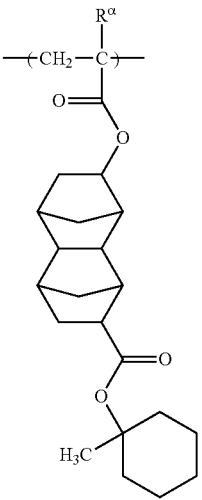

(a1-3-6)
(a1-3-9)
(a1-3-7)
(a1-3-10)
(a1-3-8)
(a1-3-11)
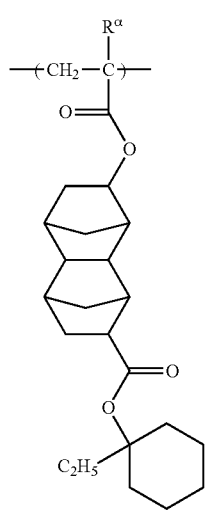
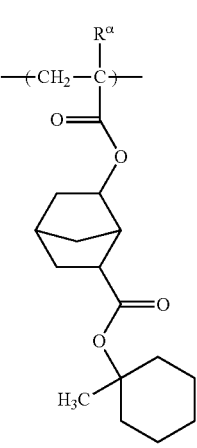
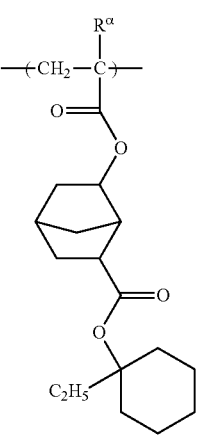
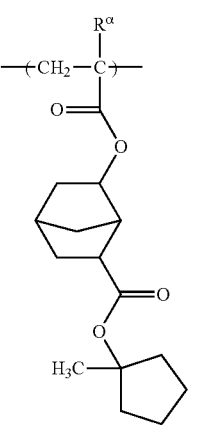

(a1-3-12) 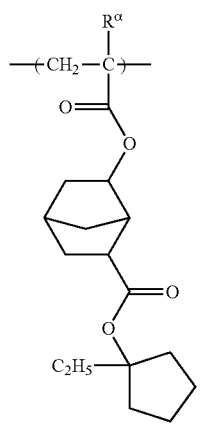
(a1-3-13) 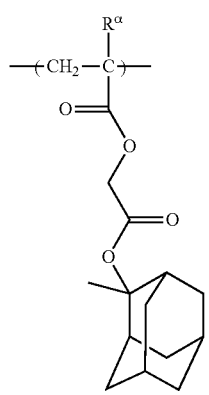
(a1-3-14) 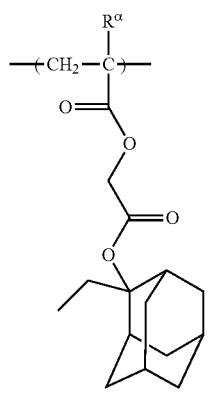
(a1-3-15) 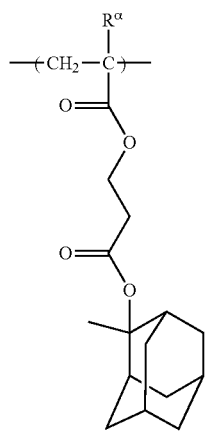
(a1-3-16) 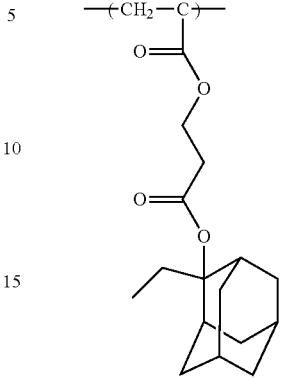
(a1-3-17) 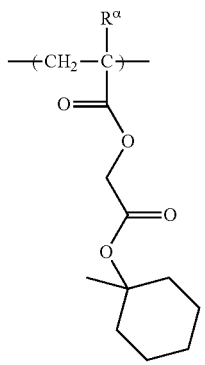
(a1-3-18) 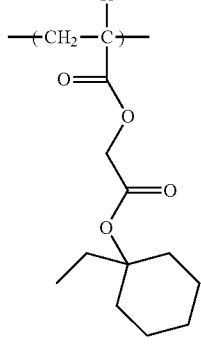
[Chemical Formula 21.]
(a1-3-19) 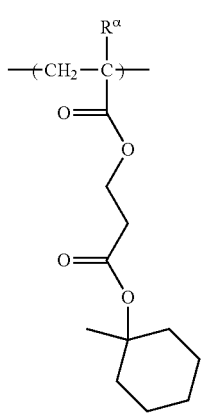

(a1-3-20)
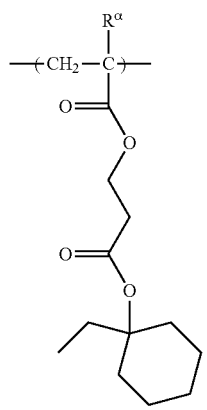
(a1-3-21)
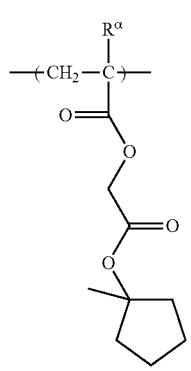
(a1-3-22)
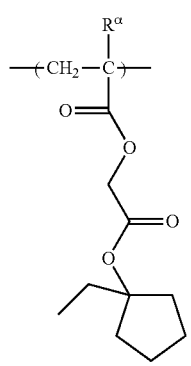
(a1-3-23)
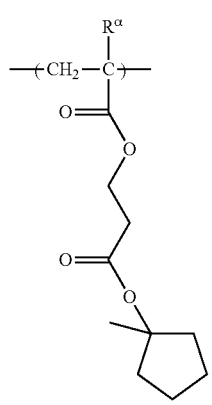
(a1-3-24)
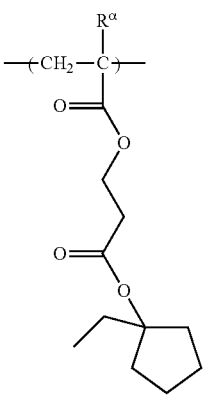
[Chemical Formula 22.]
(a1-3-25)
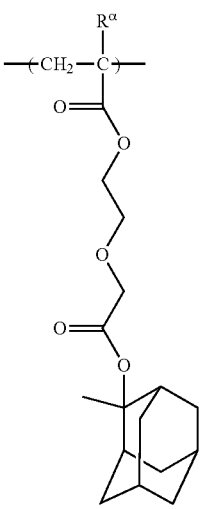
(a1-3-26)
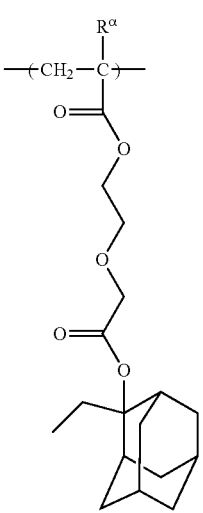

(a1-3-27) 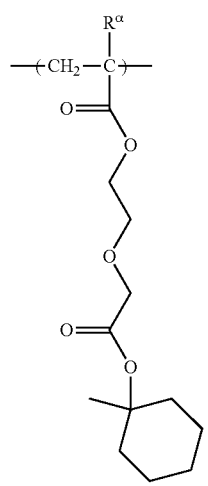
(a1-3-28) 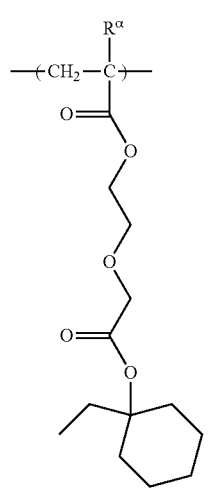
(a1-3-29) 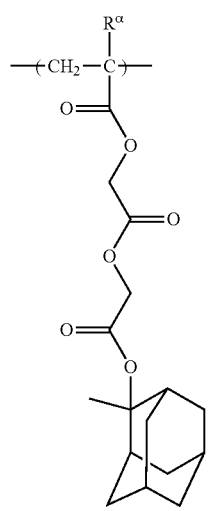
(a1-3-30) 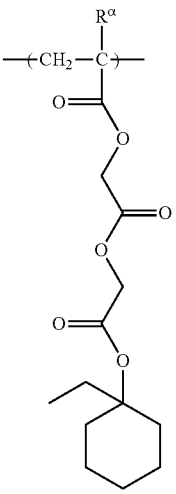
(a1-3-31) 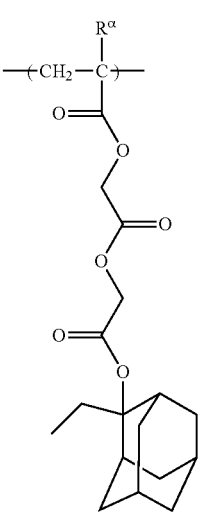
(a1-3-32) 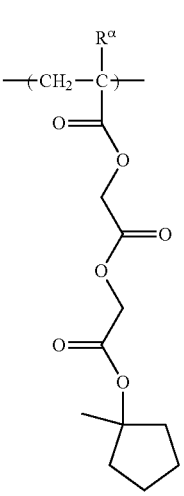

[Chemical Formula 23.]

(a1-4-1)

(a1-4-2)

(a1-4-3)

(a1-4-4)

(a1-4-5)

(a1-4-6)

(a1-4-7)
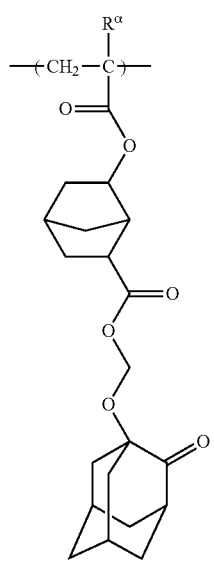
(a1-4-9)
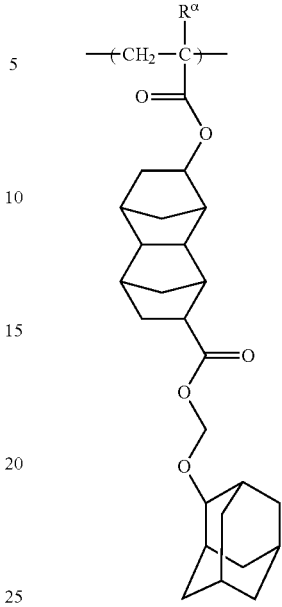
(a1-4-8)
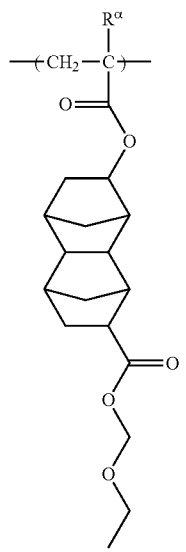
(a1-4-10)
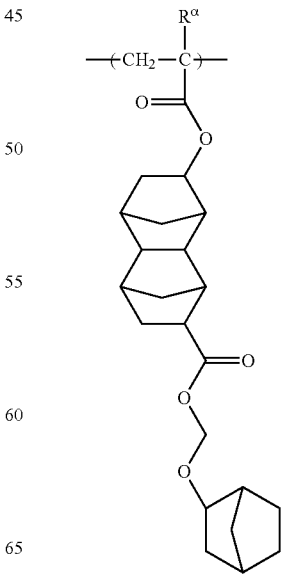

(a1-4-11)
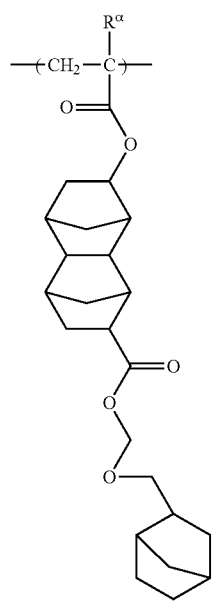
(a1-4-12)
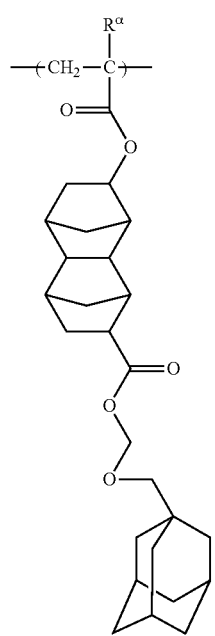
(a1-4-13)
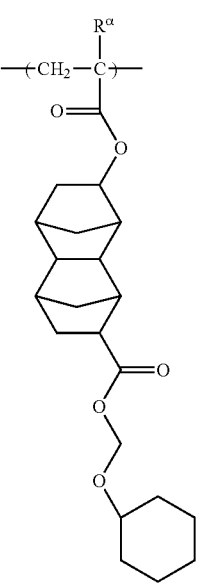
(a1-4-14)
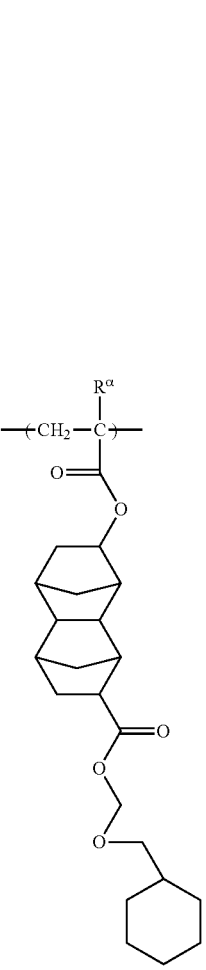

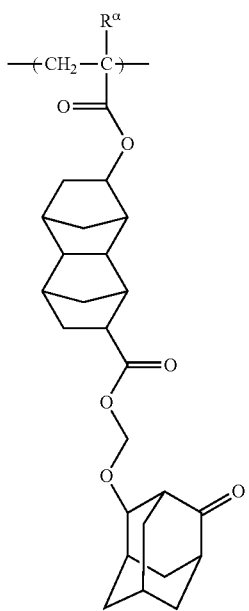

As the structural unit (a1), one type of structural unit may be used alone, or two or more types of structural units may be used in combination.

Among these, structural units represented by general formula (a1-1), (a1-2) or (a1-3) are preferable. More specifically, at least one structural unit selected from the group consisting of structural units represented by formulas (a1-1-1) to (a-1-1-4), (a1-1-20) to (a1-1-23), (a1-2-1) to (a1-2-24) and (a1-3-25) to (a1-3-28) is more preferable.

Further, as the structural unit (a1), structural units represented by general formula (a1-0-01) shown below which includes the structural units represented by formulas (a1-1-1) to (a1-1-3) and (a1-1-26), structural units represented by general formula (a1-1-02) shown below which includes the structural units represented by formulas (a1-1-16), (a1-1-17) and (a1-1-20) to (a1-1-23), structural units represented by general formula (a1-3-01) shown below which include the structural units represented by formulas (a1-3-25) and (a1-3-26), structural units represented by general formula (a1-3-02) shown below which include the structural units represented by formulas (a1-3-27) and (a1-3-28), and structural units represented by general formula (a1-0-03) shown below which include the structural units represented by formulas (a1-3-29) and (a1-3-30) are also preferable.

[Chemical Formula 24.]

(a1-1-01)

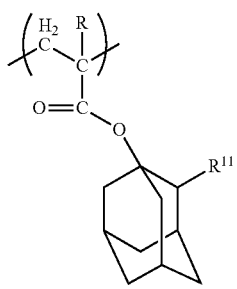

(a1-1-02)

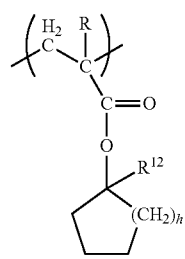

In the formulas, each R independently represents a hydrogen atom, an alkyl group of 1 to 5 carbon atoms or a halogenated alkyl group of 1 to 5 carbon atoms; $R^{11}$ represents an alkyl group of 1 to 5 carbon atoms; $R^{12}$ represents an alkyl group of 1 to 7 carbon atoms; and h represents an integer of 1 to 6.

In general formula (a1-0-01), R is the same as defined above. The alkyl group of 1 to 5 carbon atoms for $R^{11}$ is the same as defined for the alkyl group of 1 to 5 carbon atoms for R, and a methyl group, an ethyl group or an isopropyl group is preferable.

In general formula (a1-1-02), R is the same as defined above. The alkyl group of 1 to 5 carbon atoms for $R^{12}$ is the same as defined for the alkyl group of 1 to 5 carbon atoms for R, and a methyl group, an ethyl group or an isopropyl group is preferable. h is preferably 1 or 2, and most preferably 2.

[Chemical Formula 25.]

(a1-3-01)

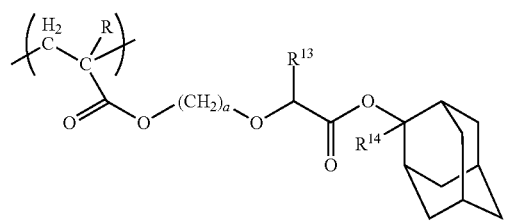

In the formula, R represents a hydrogen atom, an alkyl group of 1 to 5 carbon atoms or a halogenated alkyl group of 1 to 5 carbon atoms; $R^{14}$ is the same as defined above; $R^{13}$ represents a hydrogen atom or a methyl group; and a represents an integer of 1 to 10.

[Chemical Formula 26.]

(a1-3-02)

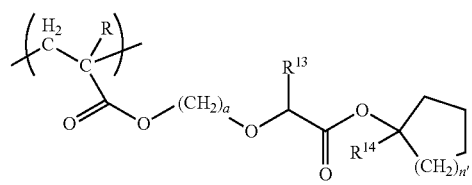

In the formula, R represents a hydrogen atom, an alkyl group of 1 to 5 carbon atoms or a halogenated alkyl group of 1 to 5 carbon atoms; $R^{14}$ is the same as defined above; $R^{13}$ represents a hydrogen atom or a methyl group; a represents an integer of 1 to 10; and n' represents an integer of 1 to 6.

[Chemical Formula 27.]

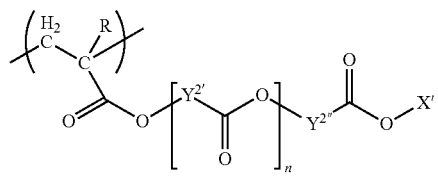

(a1-3-03)

In the formula, R is the same as defined above; each of $Y^{2\prime}$ and $Y^{2\prime\prime}$ independently represents a divalent linking group; X' represents an acid dissociable group; and n represents an integer of 0 to 3.

In general formulas (a1-3-01) to (a1-3-03), R is the same as defined above.

$R^{13}$ is preferably a hydrogen atom.

n' is preferably 1 or 2, and most preferably 2.

a is preferably an integer of 1 to 8, more preferably an integer of 2 to 5, and most preferably 2.

As the divalent linking group for $Y^{2\prime}$ and $Y^{2\prime\prime}$, the same groups as those described above for $Y^2$ in general formula (a1-3) can be used.

As $Y^{2\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2\prime\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable group for X', the same groups as those described above can be used. X' is preferably a tertiary alkyl ester-type acid dissociable group, more preferably the aforementioned group (i) which has a tertiary carbon atom on the ring structure of a monovalent aliphatic cyclic group. Among the aforementioned groups (i), a group represented by general formula (1-1) above is preferable.

n represents an integer of 0 to 3, preferably an integer of 0 to 2, more preferably 0 or 1, and most preferably 1.

In the component (A1), the amount of the structural unit (a1) based on the combined total of all structural units constituting the component (A1) is preferably 5 to 80 mol %, more preferably 10 to 80 mol %, and still more preferably 15 to 75 mol %. When the amount of the structural unit (a1) is at least as large as the lower limit of the above-mentioned range, a pattern can be easily formed using a resist composition prepared from the component (A1). On the other hand, when the amount of the structural unit (a1) is no more than the upper limit of the above-mentioned range, a good balance can be achieved with the other structural units.

(Structural Unit (a2))

The structural unit (a2) is a structural unit derived from an acrylate ester containing a lactone-containing cyclic group and may have the hydrogen atom bonded to the carbon atom on the α-position substituted with a substituent.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include a group in which one hydrogen atom has been removed from a 4- to 6-membered lactone ring, such as a group in which one hydrogen atom has been removed from β-propiolatone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 28.]

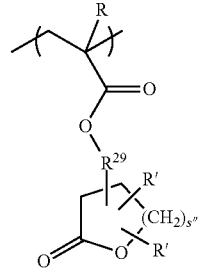

(a2-1)

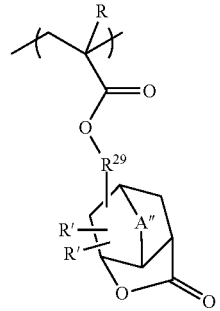

(a2-2)

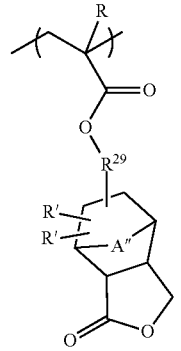

(a2-3)

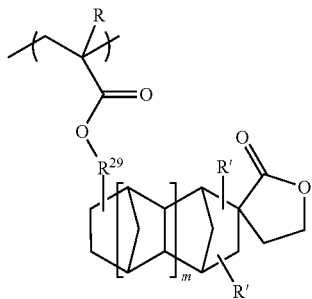

(a2-4)

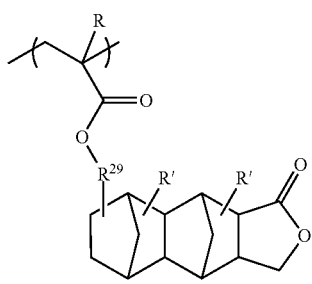

(a2-5)

In the formulas, R represents a hydrogen atom, an alkyl group of 1 to 5 carbon atoms or a halogenated alkyl group of 1 to 5 carbon atoms; each R' independently represents a hydrogen atom, an alkyl group of 1 to 5 carbon atoms, an alkoxy group of 1 to 5 carbon atoms or —COOR", wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined for R in the structural unit (a1).

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group.

In terms of industrial availability, R' is preferably a hydrogen atom.

The alkyl group for R" may be any of linear, branched or cyclic.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

A" is preferably an alkylene group of 1 to 5 carbon atoms, an oxygen atom (—O—) or a sulfur atom (—S—), and more preferably an alkylene group of 1 to 5 carbon atoms or —O—. As the alkylene group of 1 to 5 carbon atoms, a methylene group or a dimethylethylene group is preferable, and a methylene group is particularly desirable.

$R^{29}$ represents a single bond or a divalent linking group. As examples of the divalent linking group, the same divalent linking groups as those described above for X in the aforementioned formula (c1) can be given. Among these, an alkylene group, an ester bond (—C(=O)—O—) or a combination of these is preferable. The alkylene group as a divalent linking group for $R^{29}$ is preferably a linear or branched alkylene group. Specific examples include the same linear alkylene groups and branched alkylene groups as those described above for the aliphatic hydrocarbon group represented by Y.

As $R^{29}$, a single bond or —$R^{29'}$—C(=O)—O— (in the formula, $R^{29'}$ represents a linear or branched alkylene group) is particularly desirable.

The linear or branched alkylene group for $R^{29'}$ preferably has 1 to 10 carbon atoms, more preferably 1 to 8, still more preferably 1 to 5, still more preferably 1 to 3, and most preferably 1 or 2.

As the linear alkylene group for $R^{29'}$, a methylene group or an ethylene group is preferable, and a methylene group is particularly desirable. As the branched alkylene group for $R^{29'}$, an alkylmethylene group or an alkylethylene group is preferable, and —CH(CH$_3$)—, —C(CH$_3$)$_2$— or —C(CH$_3$)$_2$CH$_2$— is particularly desirable.

In formula (a2-1), s" is preferably 1 or 2.

Specific examples of structural units represented by general formulas (a2-1) to (a2-5) are shown below. In the formulas shown below, $R^\alpha$ represents a hydrogen atom, a methyl group or a trifluoromethyl group.

[Chemical Formula 29.]

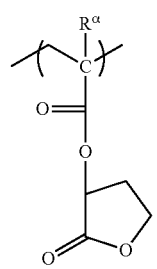

(a2-1-1)

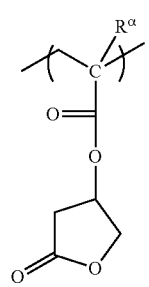

(a2-1-2)

(a2-1-3) 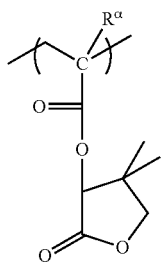
(a2-1-4) 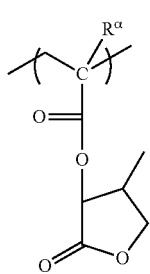
(a2-1-5) 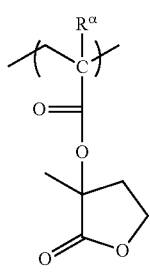
(a2-1-6) 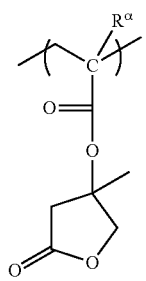
(a2-1-7) 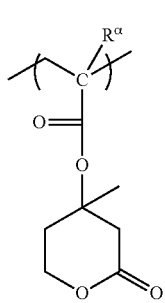
(a2-1-8) 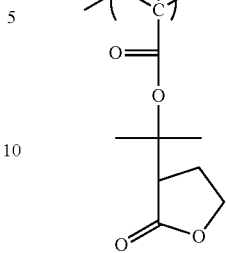
(a2-1-9) 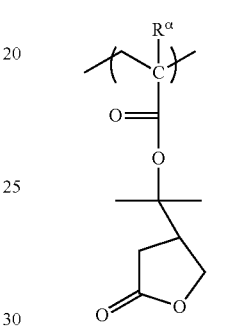
(a2-1-10) 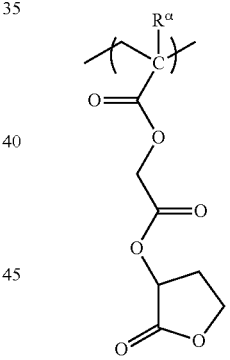
(a2-1-11) 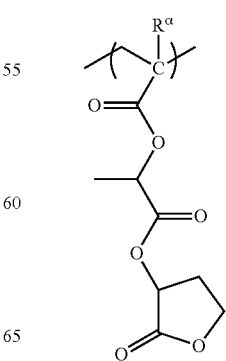

(a2-1-12)
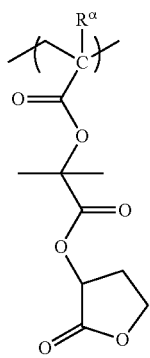
(a2-1-13)
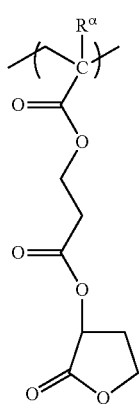
[Chemical Formula 30.]
(a2-2-1)
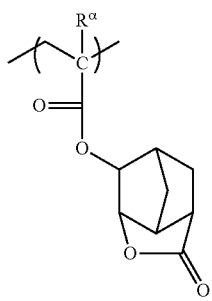
(a2-2-2)
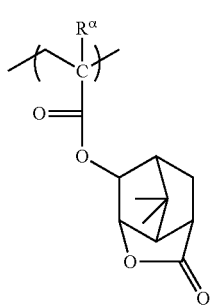
(a2-2-3)
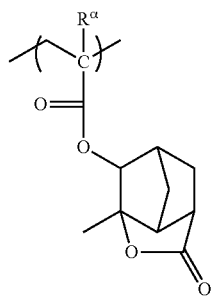
(a2-2-4)
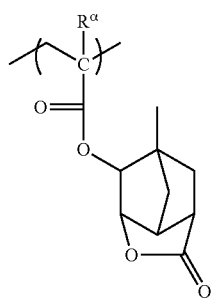
(a2-2-5)
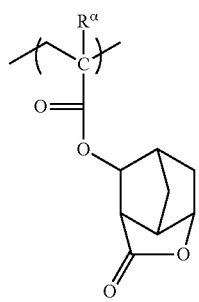
(a2-2-6)
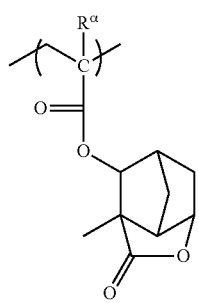
(a2-2-7)
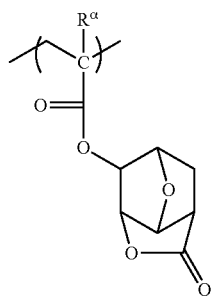

(a2-2-8)
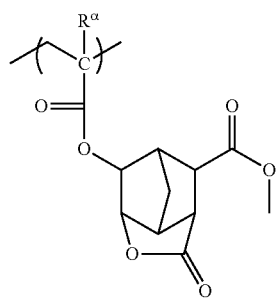
(a2-2-9)
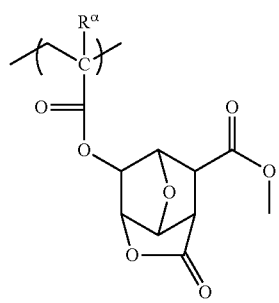
(a2-2-10)
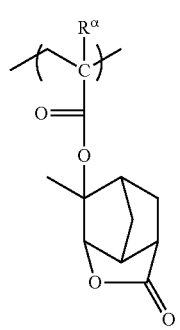
(a2-2-11)
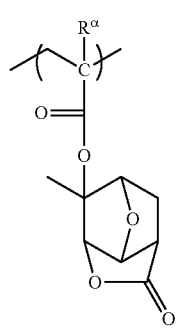
(a2-2-12)
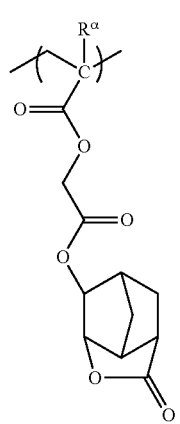
(a2-2-13)
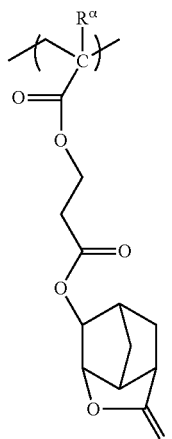
(a2-2-14)
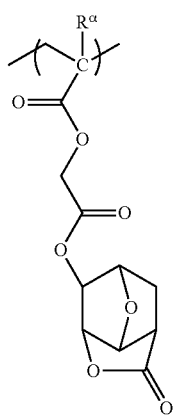
(a2-2-15)
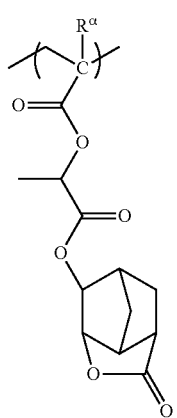

(a2-2-16)
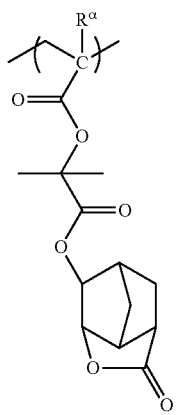
(a2-2-17)
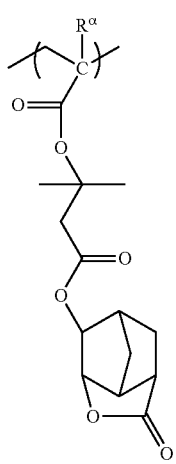
[Chemical Formula 31.]
(a2-3-1)
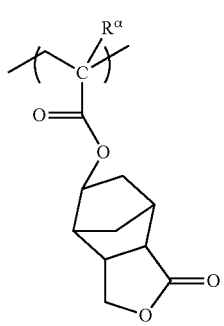
(a2-3-2)
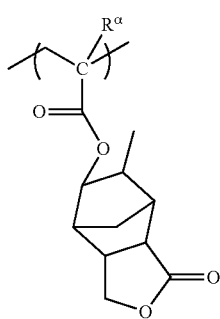
(a2-3-3)
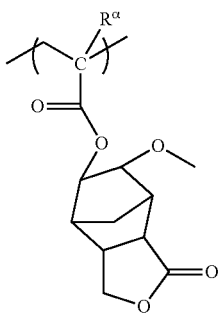
(a2-3-4)
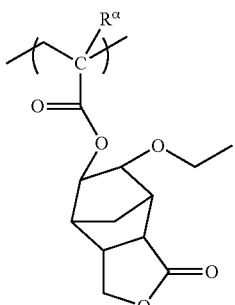
(a2-3-5)
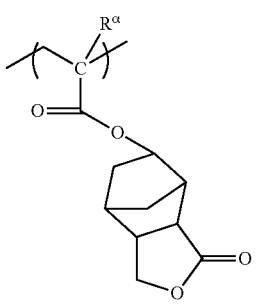
(a2-3-6)
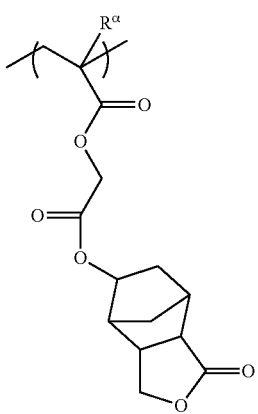

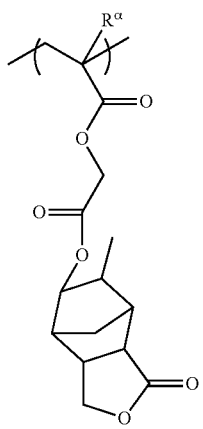 (a2-3-7)
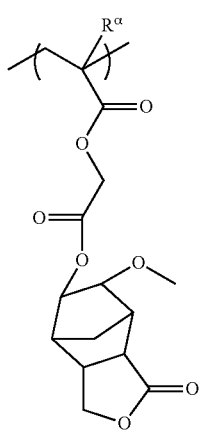 (a2-3-8)
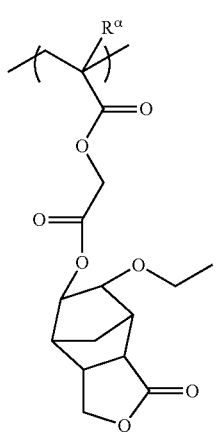 (a2-3-9)
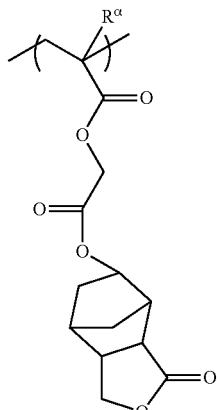 (a2-3-10)
[Chemical Formula 32.]
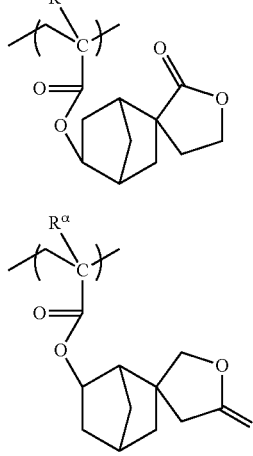
(a2-4-1)
(a2-4-2)
(a2-4-3)
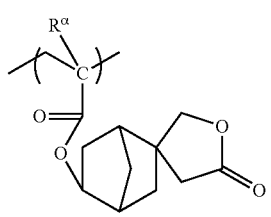 (a2-4-4)
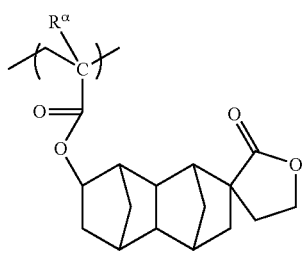 (a2-4-5)

-continued
(a2-4-6)
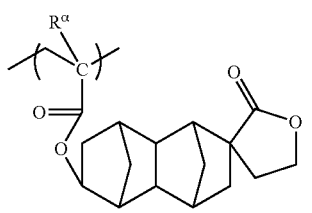
(a2-4-7)
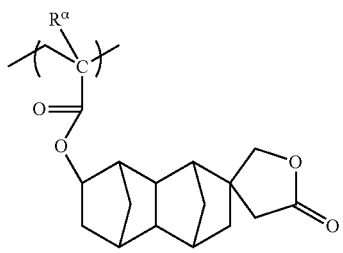
(a2-4-8)
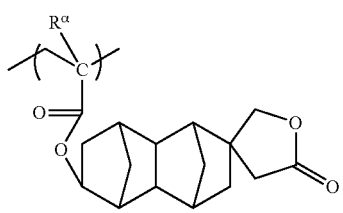
(a2-4-9)
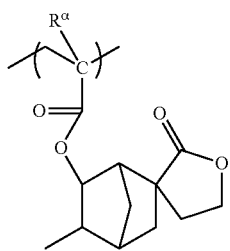
(a2-4-10)
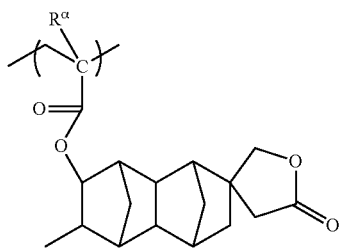
(a2-4-11)
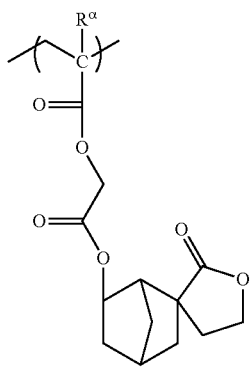
-continued
(a2-4-12)
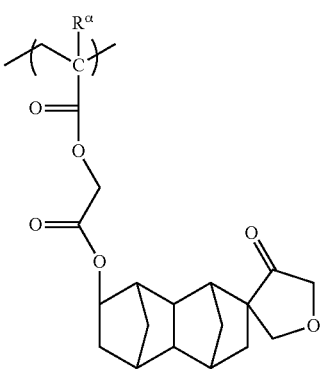
[Chemical Formula 33.]
(a2-5-1)
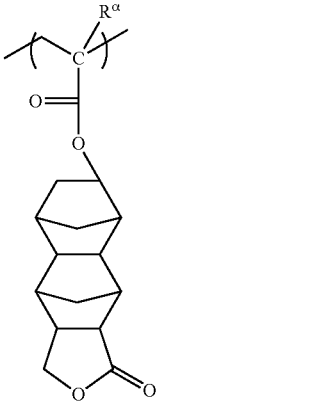
(a2-5-2)
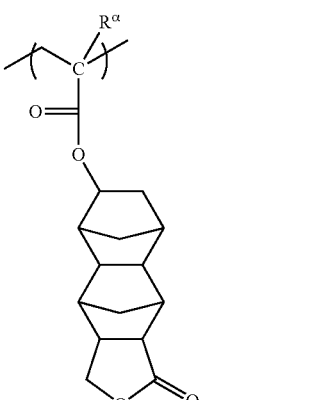
(a2-5-3)
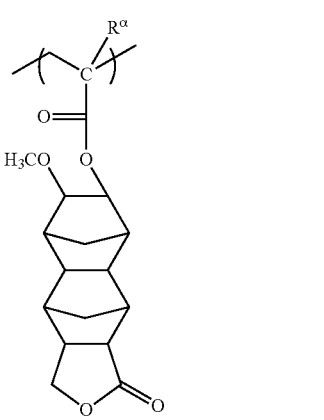

(a2-5-4)

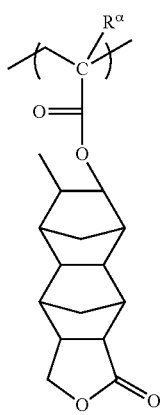

(a2-5-5)

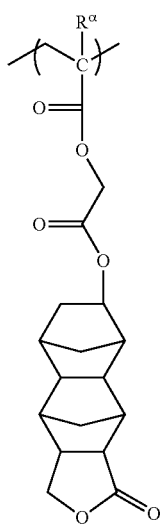

(a2-5-6)

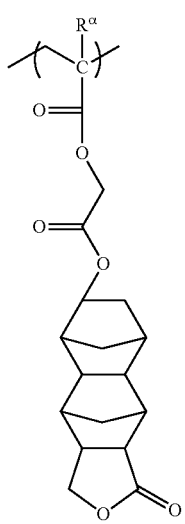

In the component (A1), as the structural unit (a2), one type of structural unit may be used, or two or more types may be used in combination.

As the structural unit (a2) within the component (A1), it is preferable to include at least one structural unit selected from the group consisting of structural units represented by the aforementioned general formulas (a2-1) to (a2-5), more preferably at least one structural unit selected from the group consisting of structural units represented by the aforementioned general formulas (a2-1) to (a2-3), and most preferably at least one structural unit selected from the group consisting of structural units represented by the aforementioned general formulas (a2-1) and (a2-3).

In terms of improving the adhesion between a substrate and a resist film formed using a positive resist composition containing the component (A1) and increasing the compatibility with a developing solution, the amount of the structural unit (a2) within the component (A1), based on the combined total of all structural units constituting the component (A1) is preferably 5 to 70 mol %, more preferably 10 to 65 mol %, still more preferably 15 to 65 mol %, and most preferably 20 to 60 mol %. By ensuring the above-mentioned range, MEF and the pattern shape can be further improved, and CDU can also be improved.

(Structural Unit (a3))

The structural unit (a3) is a structural unit derived from an acrylate ester containing a polar group-containing aliphatic hydrocarbon group and may have the hydrogen atom bonded to the carbon atom on the α-position substituted with a substituent.

When the component (A1) includes the structural unit (a3), the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and polycyclic aliphatic hydrocarbon groups (polycyclic groups).

These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 34.]

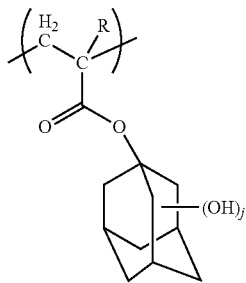
(a3-1)

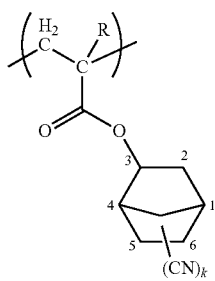
(a3-2)

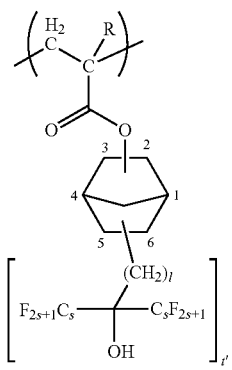
(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In general formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkylalcohol is preferably bonded to the 5th or 6th position of the norbornyl group.

As the structural unit (a3), one type of structural unit may be used, or two or more types may be used in combination.

In the component (A1), the amount of the structural unit (a3) based on the combined total of all structural units constituting the component (A1) is preferably 1 to 50 mol %, more preferably 3 to 45 mol %, and still more preferably 3 to 40 mol %. When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Other Structural Units)

The component (A1) may also have a structural unit other than the above-mentioned structural units (a1) to (a3) (hereafter, referred to as "structural unit (a4)").

As the structural unit (a4), any other structural unit which cannot be classified as one of the above structural units (a1) to (a3) can be used without any particular limitation, and any of the multitude of conventional structural units used within resist resins for ArF excimer lasers or KrF excimer lasers (and particularly for ArF excimer lasers) can be used.

Preferable examples of the structural unit (a4) include a structural unit derived from an acrylate ester which contains a non-acid-dissociable aliphatic polycyclic group and may have the hydrogen atom bonded to the carbon atom on the α-position substituted with a substituent, a structural unit derived from a styrene monomer and a structural unit derived from a vinylnaphthalene monomer. Examples of this polycyclic group include the same groups as those described above in relation to the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 35.]

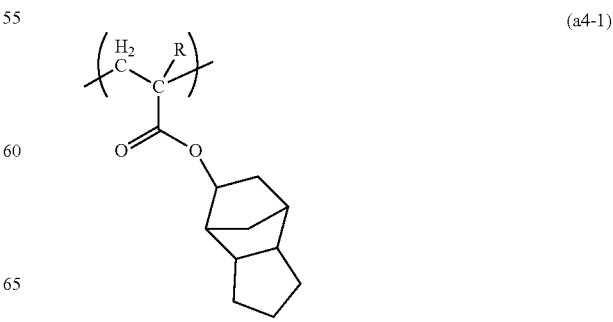
(a4-1)

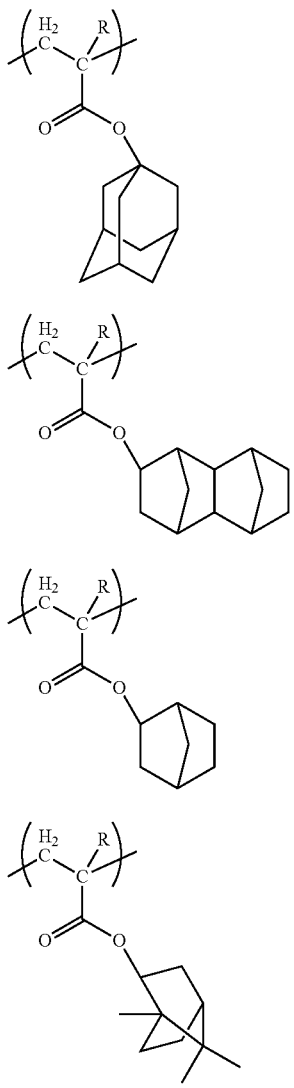

In the formulas, R is the same as defined above.

As the structural unit (a4), one type of structural unit may be used, or two or more types may be used in combination.

When the structural unit (a4) is included in the component (A1), the amount of the structural unit (a4) based on the combined total of all structural units constituting the component (A1) is preferably 1 to 20 mol %, more preferably 1 to 15 mol %, and still more preferably 1 to 10 mol %.

The component (A1) is preferably a copolymer containing the structural unit (a1).

Examples of such copolymers include a copolymer consisting of the structural units (a1) and (a3), a copolymer consisting of the structural units (a1) and (a2), and a copolymer consisting of the structural units (a1), (a2) and (a3).

In the present invention, as the component (A1), a copolymer that includes a combination of structural units represented by general formula (A1-11) shown below is particularly desirable. In general formula shown below, R, R$^{29}$, R', A", s", R$^{11}$ and j are the same as defined above, and the plurality of R and R$^{29}$ are the same or different.

[Chemical Formula 36.]

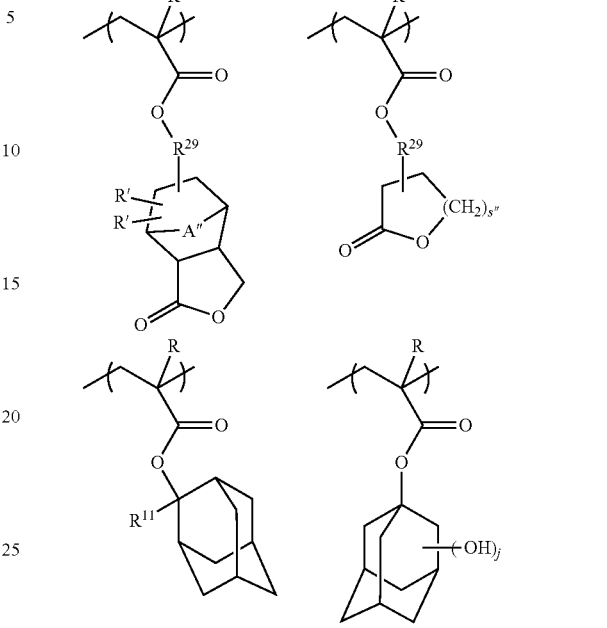

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,500 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (A1) is not particularly limited, but is preferably 1.0 to 5.0, more preferably 1.0 to 3.0, and most preferably 1.2 to 2.5.

Here, Mn is the number average molecular weight.

In the component (A), as the component (A1), one type may be used, or two or more types of compounds may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved.

[Component (A2)]

As the component (A2), it is preferable to use a compound that has a molecular weight of at least 500 and less than 2,500, contains a hydrophilic group, and also contains an acid dissociable group described above in connection with the component (A1).

Specific examples include compounds containing a plurality of phenol skeletons in which a part of the hydrogen atoms within hydroxyl groups have been substituted with the aforementioned acid dissociable groups.

Examples of the component (A2) include low molecular weight phenolic compounds in which a portion of the hydroxyl group hydrogen atoms have been substituted with an aforementioned acid dissociable group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1-bis(4-hydroxyphenyl)ethyl]benzene, and dimers, trimers, tetramers, pentamers and hexamers of formalin condensation products of phenols such as phenol, m-cresol, p-cresol and xylenol. Needless to say, the low molecular weight phenol compound is not limited to these examples. In particular, a phenol compound having 2 to 6 triphenylmethane skeletons is preferable in terms of resolution and LWR.

Also, there are no particular limitations on the acid dissociable group, and suitable examples include the groups described above.

As the component (A2), one type of resin may be used, or two or more types of resins may be used in combination.

In the resist composition, as the component (A), one type may be used, or two or more types of compounds may be used in combination.

Of the examples shown above, as the component (A), it is preferable to use one containing the component (A1).

In the resist composition, the amount of the component (A) can be appropriately adjusted depending on the thickness of the resist film to be formed, and the like.

<Component (B)>

As the component (B), there is no particular limitation, and any of the known acid generators used in conventional chemically amplified resist compositions can be used. Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (b-1) or (b-2) shown below can be used.

[Chemical Formula 37.]

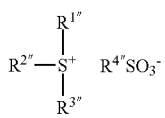
(b-1)

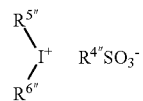
(b-2)

In the formulas, $R^{1'''}$ to $R^{3'''}$, $R^{5'''}$ and $R^{6'''}$ are the same as defined above; and $R^{4'''}$ represents an alkyl group, a halogenated alkyl group, an aryl group or an alkenyl group which may have a substituent.

In general formula (b-1), $R^{1'''}$ to $R^{3'''}$ are respectively the same as defined for $R^{1'''}$ to $R^{3'''}$ in general formula (c-1).

In general formula (b-1), $R^{5'''}$ and $R^{6'''}$ are respectively the same as defined for $R^{5'''}$ and $R^{6'''}$ in general formula (c-2).

$R^{4'''}$ represents an alkyl group, a halogenated alkyl group, an aryl group or an alkenyl group which may have a substituent.

The alkyl group for $R^{4'''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As an example of the halogenated alkyl group for $R^{4'''}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

The aryl group for $R^{4'''}$ is preferably an aryl group of 6 to 20 carbon atoms.

The alkenyl group for $R^{4'''}$ is preferably an alkenyl group of 2 to 10 carbon atoms.

With respect to $R^{4'''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4'''}$ may have one substituent, or two or more substituents.

Examples of the substituent include a halogen atom, a hetero atom, an alkyl group, and a group represented by the formula $X^{01}$-$Q^{1}$- (in the formula, $Q^{1}$ represents a divalent linking group containing an oxygen atom; and $X^{01}$ represents a hydrocarbon group of 3 to 30 carbon atoms which may have a substituent).

Examples of halogen atoms and alkyl groups as substituents for $R^{4'''}$ include the same halogen atoms and alkyl groups as those described above with respect to the halogenated alkyl group for $R^{4'''}$.

Examples of hetero atoms include an oxygen atom, a nitrogen atom, and a sulfur atom.

In the group represented by formula $X^{01}$-$Q^{1}$-, $Q^{1}$ represents a divalent linking group containing an oxygen atom.

$Q^{1}$ may contain an atom other than oxygen. Examples of atoms other than oxygen include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group.

Specific examples of the combinations of the aforementioned non-hydrocarbon, hetero atom-containing linking groups and an alkylene group include —$R^{91}$—O—, —$R^{92}$—O—C(=O)—, —C(=O)—O—$R^{93}$—O—C(=O)— (in the formulas, each of $R^{91}$ to $R^{93}$ independently represents an alkylene group).

The alkylene group for $R^{91}$ to $R^{93}$ is preferably a linear or branched alkylene group, and preferably has 1 to 12 carbon atoms, more preferably 1 to 5, and most preferably 1 to 3.

Specific examples of alkylene groups include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

$Q^1$ is preferably a divalent linking group containing an ester linkage or ether linkage, and more preferably a group of —$R^{91}$—O—, —$R^{92}$—O—C(=O)— or —C(=O)—O—$R^{93}$—O—C(=O)—.

In the group represented by the formula $X^{01}$-$Q^1$-, the hydrocarbon group for $X^{01}$ may be either an aromatic hydrocarbon group or an aliphatic hydrocarbon group.

The aromatic hydrocarbon group is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for $X^{01}$ may be either a saturated aliphatic hydrocarbon group, or an unsaturated aliphatic hydrocarbon group. Further, the aliphatic hydrocarbon group may be linear, branched or cyclic.

In the aliphatic hydrocarbon group for $X^{01}$, part of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom.

As the "hetero atom" for $X^{01}$, there is no particular limitation as long as it is an atom other than carbon and hydrogen. Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting part of the carbon atoms include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L5) and (S1) to (S4) shown below.

[Chemical Formula 38.]

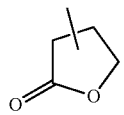 (L1)

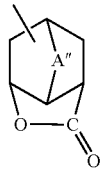 (L2)

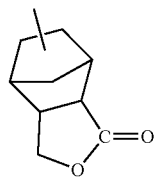 (L3)

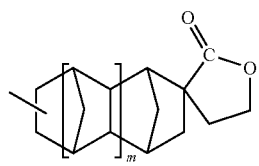 (L4)

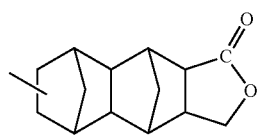 (L5)

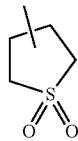 (S1)

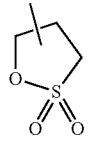 (S2)

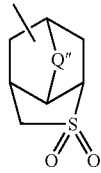 (S3)

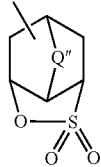 (S4)

In the formula, Q" represents an alkylene group of 1 to 5 carbon atoms, —O—, —S—, —O—R$^{94}$— or —S—R$^{95}$—

(wherein each of $R^{94}$ and $R^{95}$ independently represents an alkylene group of 1 to 5 carbon atoms); and m represents 0 or 1.

As the alkylene group for Q", $R^{94}$ and $R^{95}$, the same alkylene groups as those described above for $R^{91}$ to $R^{93}$ can be used.

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

Among these, as $X^{01}$, a cyclic group which may have a substituent is preferable. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by the aforementioned formulas (L2) to (L5), (S3) and (S4) are preferable.

In the present invention, $R^{4'''}$ preferably has $X^{01}$-$Q^1$- as a substituent. In such a case, $R^{4'''}$ is preferably a group represented by the formula $X^{01}$-$Q^1$-$Y^{01}$- (in the formula, $Q^1$ and $X^{01}$ are the same as defined above; and $Y^{01}$ represents an alkylene group of 1 to 4 carbon atoms which may have a substituent, or a fluorinated alkylene group of 1 to 4 carbon atoms which may have a substituent).

In the group represented by the formula $X^{01}$-$Q^1$-$Y^{01}$—, as the alkylene group for $Y^{01}$, the same alkylene group as those described above for $Q^1$ in which the number of carbon atoms is 1 to 4 can be used.

As the fluorinated alkylene group, the aforementioned alkylene group in which part or all of the hydrogen atoms has been substituted with fluorine atoms can be used.

Specific examples of $Y^{01}$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

$Y^{01}$ is preferably a fluorinated alkylene group, and particularly preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

As $R^{4'''}$ in formula (b-2), the same groups as those mentioned above for $R^{4'''}$ in formula (b-1) can be used.

Specific examples of suitable onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts is replaced by an alkyl sulfonate, such as methanesulfonate, n-propanesulfonate, n-butanesulfonate, n-octanesulfonate, 1-adamantanesulfonate, 2-norbornanesulfonate or d-camphor-10-sulfonate; or replaced by an aromatic sulfonate, such as benzenesulfonate, perfluorobenzenesulfonate or p-toluenesulfonate.

Furthermore, onium salts in which the anion moiety of these onium salts are replaced by an anion moiety represented by any one of formulas (b1) to (b8) shown below can be used.

[Chemical Formula 39.]

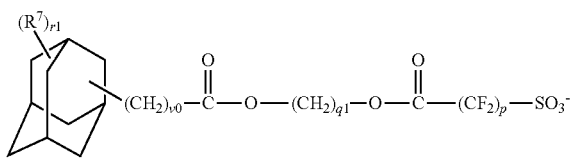
(b 1)

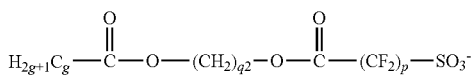
(b 2)

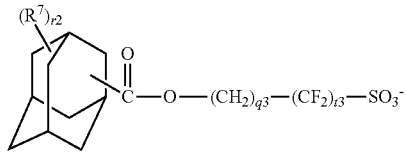
(b 3)

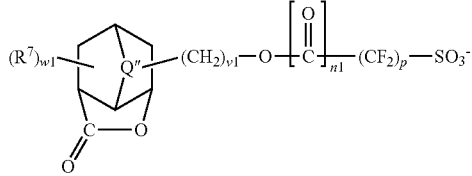
(b 4)

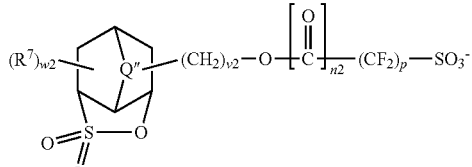
(b 5)

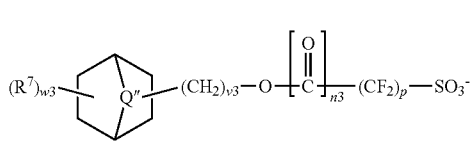
(b 6)

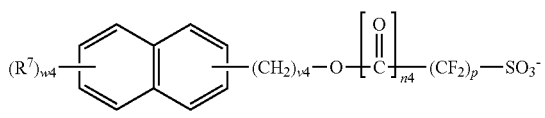
(b 7)

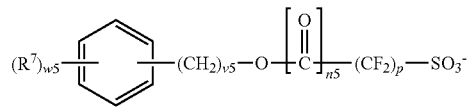
(b 8)

In the formulas, p represents an integer of 1 to 3; each of q1 and q2 independently represents an integer of 1 to 5; q3 represents an integer of 1 to 12; t3 represents an integer of 1 to 3; each of r1 and r2 independently represents an integer of 0 to 3; g represents an integer of 1 to 20; $R^7$ represents a substituent; each of n1 to n5 independently represents 0 or 1; each of v0 to v5 independently represents an integer of 0 to 3; each of w1 to w5 independently represents an integer of 0 to 3; and Q" is the same as defined above.

As the substituent for $R^7$, the same groups as those which the aforementioned aliphatic hydrocarbon group or aromatic hydrocarbon group for $X^{01}$ may have as a substituent can be used.

If there are two or more of the $R^7$ group, as indicated by the values r1, r2, and w1 to w5, then the two or more of the $R^7$ groups may be the same or different from each other.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may be used.

[Chemical Formula 40.]

(b-3)

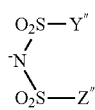
(b-4)

In the formulas, X" represents an alkylene group of 2 to 6 carbon atoms in which at least one hydrogen atom has been substituted with a fluorine atom; and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved.

The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation moiety represented by general formula (c-3) or (c-4) shown below may be used.

The anion moiety of the sulfonium salt having a cation moiety represented by general formula (c-3) or (c-4) is not particularly limited, and the same anion moieties for onium salt-based acid generators which have been proposed may be used. Examples of such anion moieties include fluorinated alkylsulfonic acid ions such as anion moieties ($R^{4"}SO_3^-$) for onium salt-based acid generators represented by general formula (b-1) or (b-2) shown above; and anion moieties represented by general formula (b-3) or (b-4) shown above.

In the present description, an oximesulfonate-based acid generator is a compound having at least one group represented by general formula (B-1) shown below, and has a feature of generating acid by irradiation. Such oximesulfonate acid generators are widely used for a chemically amplified resist composition, and can be appropriately selected.

[Chemical Formula 41.]

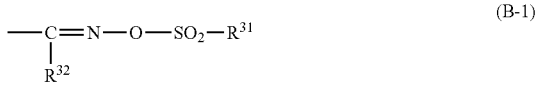

(B-1)

In the formula, each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 42.]

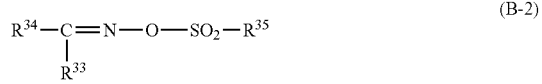

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 43.]

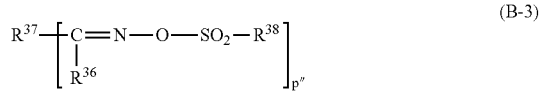

(B-3)

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate acid generators disclosed in Japanese Unexamined Patent Application, First Publication No. Hei 9-208554 (Chemical Formulas 18 and 19 shown in paragraphs [0012] to [0014]) and oxime sulfonate acid generators disclosed in WO 2004/074242A2 (Examples 1 to 40 described at pages 65 to 86) may be preferably used.

Furthermore, as preferable examples, the following can be used.

[Chemical Formula 44.]

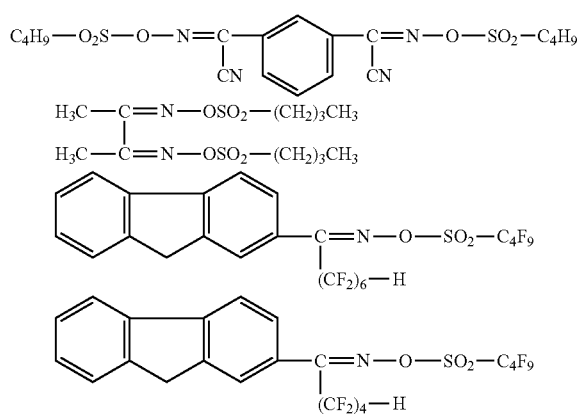

Of the aforementioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B), one type of acid generator may be used, or two or more types of acid generators may be used in combination.

Among these examples, as the component (B), it is preferable to use an onium salt having a fluorinated alkylsulfonic acid ion as the anion moiety.

In the positive resist composition, the amount of the component (B) relative to 100 parts by weight of the component (A) is preferably 0.5 to 50 parts by weight, and more preferably 1 to 40 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Component (C11)>

As described above, the component (C11) is the compound (C1) of the present invention which has an organic cation, and is explained above in relation to the compound (C1) of the present invention. In the resist composition, the component (C11) functions as an acid diffusion control agent, i.e., a quencher which traps the acid generated from the component (B) upon exposure.

In the resist composition, as the component (C11), one type of compound may be used, or two or more types of compounds may be used in combination.

The amount of the component (C11) relative to 100 parts by weight of the component (A) is preferably within a range from 0.5 to 10.0 parts by weight, and more preferably from 0.5 to 5.0 parts by weight, still more preferably from 1.0 to 4.0 parts by weight. When the amount of the component (C1) is at least as large as the lower limit of the above-mentioned range, various lithography properties (such as roughness) of the positive resist composition are improved by using in combination with the component (A1).

Further, a resist pattern having an excellent shape can be obtained. On the other hand, when the amount of the component (C1) is no more than the upper limit of the above-mentioned range, sensitivity can be maintained at a satisfactory level, and through-top becomes excellent.

<Component (D)>

It is preferable that the resist composition further includes a nitrogen-containing organic compound (D) which does not fall under the category of the component (C11) (hereafter referred to as the component (D)) as an optional component.

As the component (D), there is no particular limitation as long as it functions as an acid diffusion control agent, i.e., a quencher which traps the acid generated from the component (B) upon exposure. A multitude of these components (D) have already been proposed, and any of these known compounds may be used. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D), one type of compound may be used alone, or two or more types may be used in combination.

The component (D) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

<Component (E)>

Furthermore, in the resist composition, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added as an optional component.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferred, and salicylic acid is particularly desirable.

The component (E) is typically used in an amount within a range from 0.01 to 5.0 parts by weight, relative to 100 parts by weight of the component (A).

If desired, other miscible additives can also be added to the resist composition. Examples of such miscible additives include additive resins for improving the performance of the resist film, surfactants for improving the applicability, dissolution inhibitors, plasticizers, stabilizers, colorants, halation prevention agents, and dyes.

<Component (F)>

The resist composition may further include a fluorine additive (hereafter, referred to as "component (F)") for imparting water repellency to the resist film.

As the component (F), for example, a fluorine-containing polymeric compound described in Japanese Unexamined Patent Application, First Publication No. 2010-002870. More specifically, as the component (F), a copolymer having a structural unit represented by general formula (f1-11) shown below, and a polymer (homopolymer) consisting of a structural unit general formula (f1-11) shown below is preferable.

[Chemical Formula 45.]

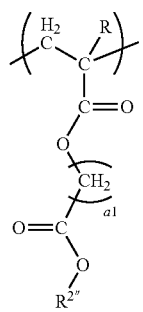

(f1-11)

In formula (f1-11), $R^{2''}$ represents an organic group containing a fluorine atom, and is preferably a hydrocarbon group containing a fluorine atom. As the hydrocarbon group containing a fluorine atom, the same groups as those described above for Rf in the aforementioned formula (c1) can be mentioned. Among these, as $R^{2''}$, a group represented by the formula "—$(CH_2)_o$—$CF_3$" is preferable (in the formula, o represents an integer of 1 to 3).

In formula (f1-11), a1 represents an integer of 1 to 5, preferably an integer of 1 to 3, and more preferably 1 or 2.

In formula (f1-11), R is the same as defined above. As R, a hydrogen atom or a methyl group is preferable.

As the component (F), one type may be used alone, or two or more types may be used in combination.

The component (F) is typically used in an amount within a range from 1 to 10 parts by weight, relative to 100 parts by weight of the component (A).

<Component (S)>

The resist composition can be produced by dissolving the materials for the resist composition in an organic solvent (hereafter, referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples of the component (S) include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

The component (S) can be used individually, or in combination as a mixed solvent.

Among these, γ-butyrolactone, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Furthermore, as the component (S), a mixed solvent of PGMEA, PGME and cyclohexanone is also preferable. The mixing ratio of such a mixed solvent is preferably PGMEA:PGME:cyclohexanone=35-55:25-45:10-30.

The amount of the component (S) is not particularly limited, and is adjusted appropriately to a concentration that enables application of a coating solution to a substrate in accordance with the thickness of the coating film. In general, the component (S) is used in an amount that yields a solid content for the resist composition that is within a range from 0.5 to 20% by weight, and preferably from 1 to 15% by weight.

Dissolving of the components for a resist composition in the component (S) can be conducted by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, or a membrane filter or the like.

As described hereinabove, the compound (C1) of the present invention is a novel compound, and can be used as a photo-decomposable base itself for a resist composition or an intermediate compound of the photo-decomposable base.

When a resist composition contains the component (C11) which is a compound (C1) having an organic cation, at unexposed portions, the anion moiety of the compound (C11) undergoes an salt exchange with a strong acid generated from the component (B) and the like upon exposure at exposed portions, thereby functioning as a quencher which suppresses diffusion of the strong acid generated from the component (B) and the like.

Further, the component (C11) is decomposed by exposure, and functions as a photoacid generator which generates a weak acid. Therefore, at exposed portions, acid is generated from not only the component (B), but also the component (C11) (thus, the component (C11) loses its function as a quencher after the photodecomposition). As a result, it is presumed that generation of acid form the component (B) and the like and deprotection reaction are promoted, thereby making a large contrast between the exposed portions and the unexposed portions, and enabling formation of a pattern with excellent shape and lithography properties while suppressing pattern collapse.

Further, by virtue of having an alicyclic group on the terminal thereof, the compound (C1) of the present invention exhibits an excellent solubility in a resist solvent. Therefore, it is presumed that the lithography properties are improved.

<<Method of Forming a Resist Pattern>>

Using the resist composition as described above, for example, a resist pattern can be formed by a method as described below.

Firstly, a resist composition of the present invention is applied to a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus, an electron lithography system or the like, the resist film is selectively exposed to an ArF excimer laser beam or an electron beam (EB) through a desired mask pattern, followed by post exposure bake (PEB) under temperature conditions of 80 to 150° C. for 40 to 120 seconds, preferably 60 to 90 seconds. Subsequently, the resist film is subjected to a developing process.

In the case of an alkali developing process, an alkali developing solution such as a 0.1 to 10% by weight aqueous solution of tetramethylammonium hydroxide (TMAH) is used to perform an alkali developing treatment.

Alternatively, in the case of a solvent developing process, an organic solvent is used to perform a developing treatment. As the organic solvent, any of the conventional organic solvents can be used which are capable of dissolving the component (A) (prior to exposure). Specific examples of the organic solvent include polar solvents such as ketone solvents, ester solvents, alcohol solvents, amide solvents and ether solvents, and hydrocarbon solvents. Among these, ester solvents are preferable. As an ester solvent, butyl acetate is preferable.

After the developing treatment, it is preferable to conduct a rinse treatment. In the case of an alkali developing process, it is preferable to conduct a water rinse using pure water. In the case of a solvent developing process, it is preferable to use a rinse liquid containing the aforementioned organic solvent.

Thereafter, drying is conducted. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays.

The resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air.

More specifically, in immersion lithography, the region between the resist film formed in the above-described manner and lens at the lowermost portion of the exposure apparatus is filled with a solvent (a immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

EXAMPLES

As follows is a description of examples of the present invention, although the scope of the present invention is by no way limited by these examples.

In the NMR analysis of the present examples, the chemical shift standard for $^1$H-NMR was tetramethylsilane (TMS), and the chemical shift standard for $^{19}$F-NMR was trichlorofluoromethane (the peak of hexafluorobenzene was regarded as −162.2 ppm).

Synthesis Example 1

Synthesis of N-[2-(adamantan-1-ylcarbonyloxy)ethyl]trifluoromethanesulfonamide 100 g (0.52 mol) of trifluoromethanesulfonamide ethanol, 108.6 g (0.54 mol) of 1-adamantanecarboxylic acid, 0.1 mol of para-toluenesulfonic acid and 500 g of toluene were added to a glass flask equipped with a thermometer and a condenser, followed by dehydration using a dean-stark dehydration apparatus under reflux. After 9 hours of reflux, about 9 ml of water was removed. The resulting reaction solution was dissolved in 500 g of ethyl acetate, and washing was conducted twice with a saturated sodium hydrogencarbonate solution, once with a 1N—HCl and once with a saturated saline solution in this order. Then, the organic phase was dried with sodium sulfate, and the solvent was distilled off under reduced pressure. The resultant was subjected to recrystallization in hexane, thereby obtaining 140 g of N-[2-(adamantan-1-ylcarbonyloxy)ethyl]trifluoromethanesulfonamide (yield: 75%, purity: 99%).

Properties of N-[2-(adamantan-1-ylcarbonyloxy)ethyl]trifluoromethanesulfonamide $^1$H NMR (Solvent: deuteriochloroform, standard: tetramethylsilane); δ=5.43-5.35 (brs, 1H), 4.20 (t, 2H, J=5.2 Hz), 3.53 (td, 2H, J=5.2 Hz), 2.08-1.98 (brs, 3H), 1.91-1.87 (brs, 6H), 1.75-1.67 (brs, 6H).
$^{19}$F NMR (Solvent: deuteriochloroform, standard: tetramethylsilane); δ=−77.8 (s, 3F).

From the analysis results shown above, it was confirmed that the obtained compound was N-[2-(adamantan-1-ylcarbonyloxy)ethyl]trifluoromethanesulfoneamide represented by formula (i) shown below.

[Chemical Formula 46.]

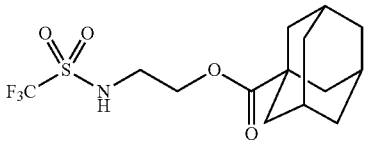

(i)

Synthesis Example 2

Synthesis of triphenylsulfonium N-[2-(adamantan-1-ylcarbonyloxy)ethyl]trifluoromethanesulfoneamide 240 g (0.63 mol) of N-[2-(adamantan-1-ylcarbonyloxy)ethyl]trifluoromethanesulfonamide obtained in Synthesis Example 1 above, 800 ml of water and 800 ml of chloroform were added to a 3 L-reactor, and 240 g (0.68 mol) of a 11% NaOH solution was gradually added thereto in a dropwise manner while maintaining the internal temperature of the reactor at 0° C., followed by stirring for 30 minutes. Then, 244 g (0.71 mol) of triphenylsulfonium bromide was added thereto, followed by stirring at room temperature for 15 hours. The resultant was subjected to liquid separation, and the obtained organic phase was washed with 800 ml of water four times, followed by concentration under reduced pressure. The resulting yellow oily substance was dissolved in acetonitrile, and recrystallization was performed in isopropyl ether (IPE), thereby obtaining 360 g of triphenylsulfonium N-[2-(adamantan-1-ylcarbonyloxy)ethyl]trifluoromethanesulfonamide. The purity was 99%, and the yield was 87%.

Properties of triphenylsulfonium N-[2-(adamantan-1-ylcarbonyloxy)ethyl]trifluoromethanesulfonamide $^1$H NMR (Solvent: deuterated DMSO, standard: tetramethylsilane); δ=7.88-7.76 (m, 15H; Ph$_3$S$^+$), 3.85 (t, 2H), 3.02 (t, 2H), 2.08-1.98 (brs, 3H), 1.91-1.87 (brs, 6H), 1.75-1.67 (brs, 6H).
$^{19}$F NMR (Solvent: deuterated DMSO, standard: tetramethylsilane); δ=−75.5 (s, 3F).

From the analysis results shown above, it was confirmed that the obtained compound was triphenylsulfonium N-[2-(adamantan-1-ylcarbonyloxy)ethyl]trifluoromethanesulfonamide represented by formula (C)-1 shown below.

[Chemical Formula 47.]

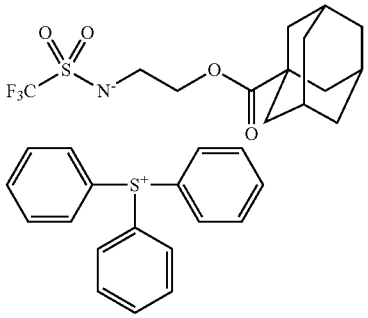

(C)-1

Examples 1 to 4, Comparative Examples 1 to 3

The components shown in Table 1 were mixed together and dissolved to obtain positive resist compositions.

TABLE 1

|  | Component (A) | Component (B) |  | Component (C) | Component (D) | Component (F) | Component (S) |
|---|---|---|---|---|---|---|---|
| Comp. Ex. 1 | (A)-1 [100] | (B)-1 [2.00] | (B)-2 [8.00] |  | (D)-1 [1.22] | (F)-1 [3.0] | (S)-1 [3000] |
| Comp. Ex. 2 | (A)-1 [100] | (B)-1 [2.00] | (B)-2 [8.00] | (C)-A [1.70] |  | (F)-1 [3.0] | (S)-1 [3000] |
| Comp. Ex. 3 | (A)-1 [100] | (B)-1 [2.00] | (B)-2 [8.00] | (C)-B [1.80] |  | (F)-1 [3.0] | (S)-1 [3000] |
| Ex. 1 | (A)-1 [100] | (B)-1 [2.00] | (B)-2 [8.00] | (C)-1 [1.06] |  | (F)-1 [3.0] | (S)-1 [3000] |
| Ex. 2 | (A)-1 [100] | (B)-1 [2.00] | (B)-2 [8.00] | (C)-1 [2.12] |  | (F)-1 [3.0] | (S)-1 [3000] |
| Ex. 3 | (A)-1 [100] | (B)-1 [2.00] | (B)-2 [8.00] | (C)-2 [2.80] |  | (F)-1 [3.0] | (S)-1 [3000] |
| Ex. 4 | (A)-1 [100] | (B)-1 [2.00] | (B)-2 [8.00] | (C)-3 [2.14] |  | (F)-1 [3.0] | (S)-1 [3000] |

In Table 1, the reference characters indicate the following. Further, the values in brackets [ ] indicate the amount (in terms of parts by weight) of the component added. The properties and the synthesis examples of compounds (C)-2 and (C)-3 are as described below.

(A)-1: polymeric compound (A)-1 shown below
(B)-1: compound (B)-1 shown below
(B)-2: compound (B)-2 shown below
(C)-A: compound (C)-A shown below
(C)-B: compound (C)-B shown below
(C)-1: the aforementioned compound (C)-1
(C)-2: compound (C)-2 shown below
(C)-3: compound (C)-3 shown below
(D)-1: tri-n-octylamine.
(F)-1: polymeric compound (F)-1 shown below
(S)-1: a mixed solvent of PGMEA/PGME/cyclohexanone=45/30/25 (weight ratio)

Properties of Compound (C)-2

$^1$H-NMR (deuterated DMSO, 400 MHz): δ(ppm)=7.76-7.82 (m, 10H, ArH), 7.59 (s, 2H, ArH), 4.55 (s, 2H, CH$_2$), 3.82-3.89 (t, 2H, CH$_2$), 3.00-3.08 (t, 2H, CH$_2$), 2.29 (m, 6H, CH$_3$), 1.48-1.93 (m, 25H, Cyclopentyl+Adamantanyl), 0.77-0.81 (t, 3H, CH$_3$)

$^{19}$F-NMR (deuterated DMSO, 376 MHz): δ(ppm)=−75.5

Properties of Compound (C)-3

$^1$H-NMR (deuterated DMSO, 400 MHz): δ(ppm)=8.28 (d, 2H, ArH), 8.12 (d, 1H, ArH), 7.88 (t, 1H, ArH), 7.80 (d, 1H, ArH), 7.62-7.74 (m, 5H, ArH), 3.82-3.89 (t, 2H, CH$_2$), 3.00-3.08 (t, 2H, CH$_2$), 1.58-1.93 (m, 15H, Adamantanyl), 1.27 (s, 9H, CH$_3$).

$^{19}$F-NMR (deuterated DMSO, 376 MHz): δ(ppm)=−75.5

Synthesis Example of Compound (C)-2

3.91 g of N-[2-(adamantan-1-ylcarbonyloxy)ethyl]trifluoromethanesulfonamide, 36 ml of water and 180 ml of chloroform were added to a reactor, and 4.4 g of a 10% NaOH solution was gradually added thereto in a dropwise manner while maintaining the internal temperature of the reactor at 0° C., followed by stirring for 10 minutes. Then, 5.42 g of PAG[A] was added thereto, followed by stirring at room temperature for 1 hour. The resultant was subjected to liquid separation, and the obtained organic phase was washed with 36 ml of water four times, followed by concentration under reduced pressure, thereby obtaining 6.7 g of a compound (C)-2.

The synthesis of the compound (C)-3 was performed in the same manner as that of the compound (C)-2.

[Chemical Formula 48.]

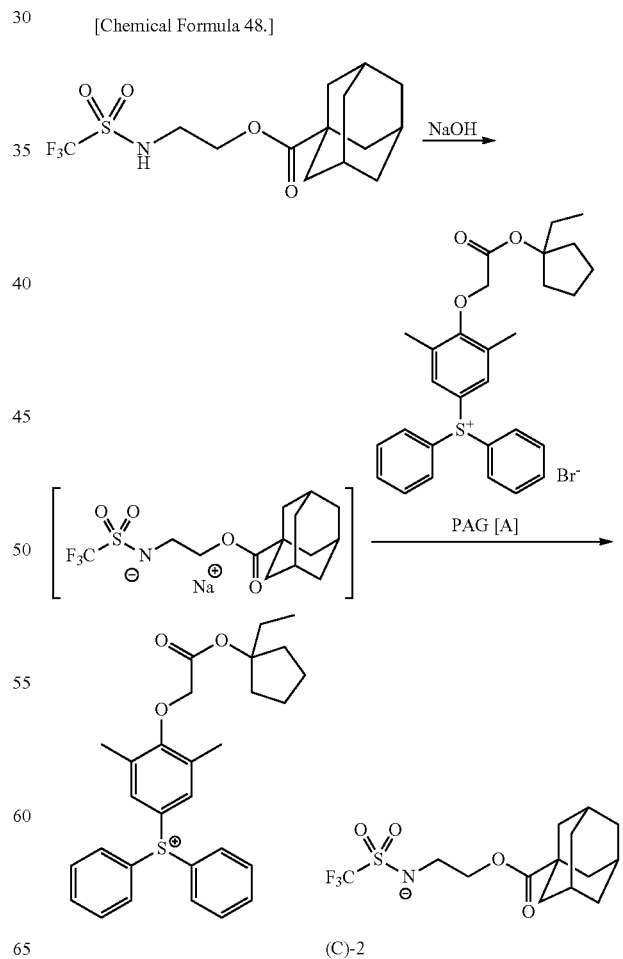

(C)-2

-continued
[Chemical Formula 49.]
(A)-1
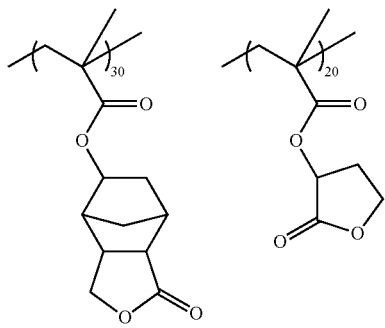
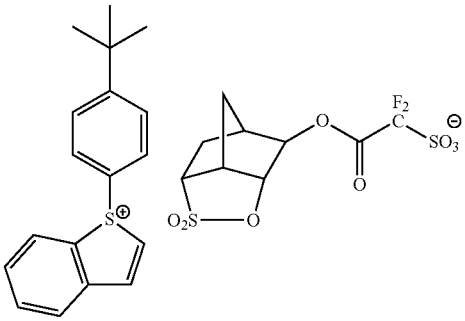
(B)-2
[Mw=9,400, Mw/Mn=1.65, the subscript numerals shown to the bottom right of the parentheses ( ) indicate the compositional ratio (molar ratio) of the copolymer]
[Chemical Formula 50.]
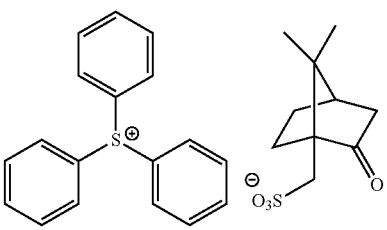
(C)-A
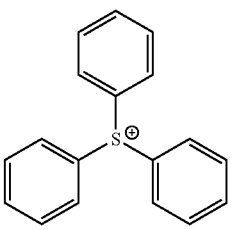
(C)-B
(C)-2
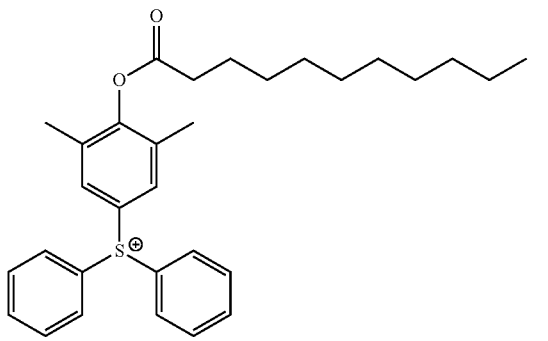
(B)-1
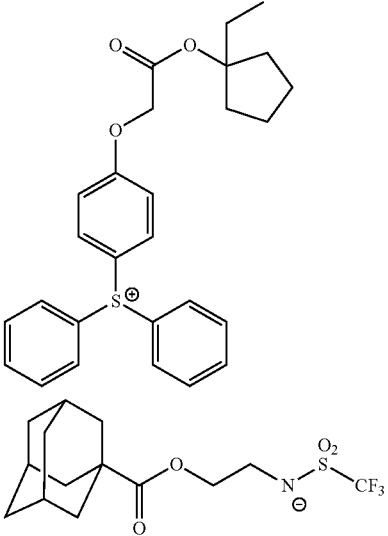

-continued

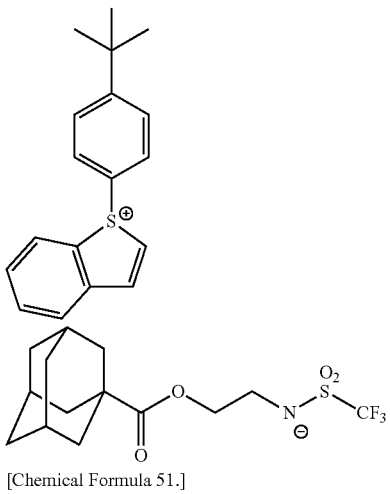

[Chemical Formula 51.]

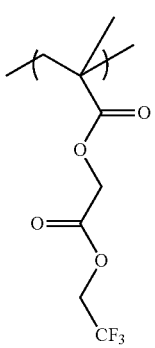

Using the obtained positive resist compositions, resist patterns were formed in the following manner, and the following evaluations were conducted.

[Formation of Resist Pattern]

An organic anti-reflection film composition (product name: ARC95, manufactured by Brewer Science Ltd.) was applied to a 12-inch silicon wafer using a spinner, and the composition was then baked at 205° C. for 90 seconds, thereby forming an organic anti-reflection film having a film thickness of 90 nm.

Then, each of the resist compositions of Examples 1 to 4 and Comparative Examples 1 to 3 was applied to the organic anti-reflection film using a spinner, and was then prebaked (PAB) on a hotplate at 120° C. for 60 seconds and dried, thereby forming a resist film having a film thickness of 100 nm.

Subsequently, the resist film was selectively irradiated with an ArF excimer laser (193 nm) through a mask pattern (6% halftone), using an ArF immersion exposure apparatus NSR-S609B (manufactured by Nikon Corporation; Dipole (in/out: 0.78/0.97) w/POLANO; immersion medium: water).

Thereafter, a post exposure bake (PEB) treatment was conducted at 115° C. for 60 seconds, followed by alkali development for 10 seconds at 23° C. in a 2.38% by weight aqueous solution of tetramethylammonium hydroxide (TMAH). Then, the resist was washed for 30 seconds with pure water, followed by drying by shaking.

Further, a post bake was conducted at 100° C. for 45 seconds.

As a result, in each of the examples, a 1:1 line and space pattern (LS pattern) having a line width of 50 nm was formed.

The optimum exposure dose Eop (mJ/cm$^2$; sensitivity) with which the LS pattern was formed was determined. The results are shown in Table 2.

[Evaluation of Line Width Roughness (LWR)]

With respect to each of the LS patterns formed with the above Eop and having a space width of 50 nm and a pitch of 100 nm, the space width at 400 points in the lengthwise direction of the space were measured using a measuring scanning electron microscope (SEM) (product name: S-9220, manufactured by Hitachi, Ltd.; acceleration voltage: 800V). From the results, the value of 3 times the standard deviation s (i.e., 3 s) was determined, and the average of the 3 s values at 400 points was calculated as a yardstick of LWR. The results are shown in Table 2.

The smaller this 3 s value is, the lower the level of roughness of the line width, indicating that a LS pattern with a uniform width was obtained.

[Evaluation of Pattern Collapse]

LS patterns were formed in the same manner as described above, except that the Eop was varied, and the line width was measured just before the pattern collapsed.

The smaller this value is, the more resistant is the resist pattern to a pattern collapse.

[Evaluation of Exposure Latitude (EL Margin)]

With respect to the above Eop, the exposure dose with which an LS pattern having a dimension of the target dimension (space width: 50 nm)±5% (i.e., 47.5 nm to 52.5 nm) was determined, and the EL margin (unit: %) was determined by the following formula. The results are shown in Table 2.

$$EL\ margin(\%) = (|E1-E2|/Eop) \times 100$$

In the formula, E1 represents the exposure dose (mJ/cm$^2$) for forming an LS pattern having a line width of 47.5 nm, and E2 represents the exposure dose (mJ/cm$^2$) for forming an LS pattern having a line width of 52.5 nm.

The larger the value of the "EL margin", the smaller the change in the pattern size by the variation of the exposure dose.

[Evaluation of Pattern Shape]

With respect to each of the 50 nm 1:1 L/S patterns formed with the above Eop, the cross-sectional shape was observed using a scanning electron microscope (SEM) (product name: S-4700, manufactured by Hitachi, Ltd.), and the cross-sectional shape was evaluated with the following criteria. The results are shown in Table 2.

A: high rectangularity and excellent shape
B: Top-rounded shape, and low rectangularity
C: T-top shaped, low rectangularity

TABLE 2

|  | Eop (mJ/cm$^2$) | LWR (nm) | Pattern collapse CD (nm) | EL (±5%) | Shape |
|---|---|---|---|---|---|
| Comp. Ex. 1 | 29.2 | 5.04 | 43.5 | 8.57 | C |
| Comp. Ex. 2 | 21.3 | 4.45 | 38.1 | 8.81 | B |
| Comp. Ex. 3 | 25.7 | 4.36 | 39.2 | 8.92 | B |
| Ex. 1 | 17.5 | 4.06 | 35.6 | 10.72 | A |
| Ex. 2 | 23.9 | 3.98 | 34.4 | 10.52 | A |
| Ex. 3 | 25.6 | 4.11 | 35.9 | 10.07 | A |
| Ex. 4 | 28.4 | 4.05 | 35.6 | 10.61 | A |

From the results shown in Table 2, it was confirmed that the resist compositions of Examples 1 to 4 were superior to the resist compositions of Comparative Examples 1 to 3 in that not only did they exhibited excellent lithography properties (such as LWR and EL margin) and excellent shape, but also pattern collapse could be suppressed.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A compound represented by general formula (c1) shown below:

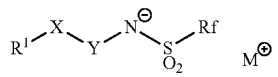

(c1)

$R^1$ represents an alicyclic group of 5 or more carbon atoms which may have a substituent; X represents a divalent linking group; Y represents a linear, branched or cyclic alkylene group or an arylene group; Rf represents a hydrocarbon group containing a fluorine atom; and $M^+$ represents an organic cation or a metal cation.

* * * * *